US012779011B2

(12) United States Patent
Knoch et al.

(10) Patent No.: US 12,779,011 B2
(45) **Date of Patent: *Nov. 3, 2026**

(54) CYCLOSPORINE FORMULATIONS FOR USE IN THE PREVENTION OR TREATMENT OF PULMONARY CHRONIC GRAFT REJECTION

(71) Applicant: BREATH THERAPEUTICS GMBH, Munich (DE)

(72) Inventors: Martin Knoch, Garmisch-Partenkirchen (DE); Oliver Denk, Münsing (DE)

(73) Assignee: BREATH THERAPEUTICS GMBH, Munich (DE)

( * ) Notice: Subject to any disclaimer, the term of this patent is extended or adjusted under 35 U.S.C. 154(b) by 553 days.

This patent is subject to a terminal disclaimer.

(21) Appl. No.: 18/353,524

(22) Filed: Jul. 17, 2023

(65) Prior Publication Data

US 2024/0016885 A1 Jan. 18, 2024

Related U.S. Application Data

(63) Continuation of application No. 17/086,254, filed on Oct. 30, 2020, now Pat. No. 11,744,872, which is a (Continued)

(30) Foreign Application Priority Data

Mar. 16, 2015 (EP) .................................... 15020035

(51) Int. Cl.

*A61K 38/13* (2006.01)
*A61K 9/00* (2006.01)

(Continued)

(52) U.S. Cl.

CPC ............ *A61K 38/13* (2013.01); *A61K 9/0053* (2013.01); *A61K 9/0078* (2013.01); *A61K 9/127* (2013.01);

(Continued)

(58) Field of Classification Search

None

See application file for complete search history.

(56) References Cited

U.S. PATENT DOCUMENTS

| | | | | |
|---|---|---|---|---|
| 8,158,110 B2 * | 4/2012 | Iacono | .................... | A61P 37/06 424/45 |
| 10,857,198 B2 * | 12/2020 | Knoch | .................... | A61K 9/19 |

(Continued)

FOREIGN PATENT DOCUMENTS

| | | | |
|---|---|---|---|
| WO | WO 03/035030 A1 | | 5/2003 |
| WO | WO 2007/065588 A1 | | 6/2007 |
| WO | 2016146645 A1 | | 9/2016 |

OTHER PUBLICATIONS

John A. Belperio, S. Samuel Weigt, Michael C. Fishbein, and Joseph P. Lynch III. "Chronic Lung Allograft Rejection Mechanisms and Therapy." Proceedings of the American Thoracic Society, vol. 6, 2009, pp. 108-121. (Year: 2009).*

(Continued)

*Primary Examiner* — Isaac Shomer

(74) *Attorney, Agent, or Firm* — Synergy IP Group AG; Lily Ackerman

(57) ABSTRACT

The invention relates to cyclosporine formulations for use in the prevention or treatment of pulmonary chronic graft rejection. In particular, the invention provides a cyclosporine liquid formulation for use as an aerosol for inhalation in a method of preventing or treating pulmonary chronic graft rejection in single lung transplanted patients. The formulation is preferably administered once or twice daily. The formulation may be aerosolized with a nebulizer that comprises features for monitoring the time, date and duration of inhalation by the patient, in order to monitor patient adherence. The formulation according to the invention may be combined with standard immunosuppressants and corticosteroids.

29 Claims, 14 Drawing Sheets

Related U.S. Application Data continuation of application No. 15/558,102, filed as application No. PCT/EP2016/055609 on Mar. 15, 2016, now Pat. No. 10,857,198.

(51) Int. Cl.

| | |
|---|---|
| ***A61K 9/127*** | (2025.01) |
| ***A61K 9/19*** | (2006.01) |
| ***A61K 45/06*** | (2006.01) |
| *A61K 47/26* | (2006.01) |

(52) U.S. Cl.

CPC ................ *A61K 9/19* (2013.01); *A61K 45/06* (2013.01); *A61K 47/26* (2013.01)

(56) References Cited

U.S. PATENT DOCUMENTS

| | | | | |
|---|---|---|---|---|
| 11,419,819 | B2 * | 8/2022 | Denk | A61K 47/26 |
| 11,484,566 | B2 * | 11/2022 | Iacono | A61P 11/00 |
| 11,744,872 | B2 * | 9/2023 | Knoch | A61K 9/0053 424/450 |
| 11,890,376 | B2 * | 2/2024 | Denk | A61K 38/13 |
| 12,178,843 | B2 * | 12/2024 | Iacono | A61K 9/0078 |
| 12,263,247 | B2 * | 4/2025 | Denk | A61K 38/13 |
| 2002/0006901 | A1 | 1/2002 | Iacono | |
| 2009/0169607 | A1 | 7/2009 | Keller et al. | |
| 2012/0285236 | A1 | 11/2012 | Haartsen et al. | |
| 2013/0177626 | A1 | 7/2013 | Keller et al. | |

OTHER PUBLICATIONS

Sam Howard, Alexandra Lang, Mitesh Patel, Sarah Sharples, Dominick Shaw. "Electronic Monitoring of Adherence to Inhaled Medication in Asthma." Current Respiratory Medicine Reviews, vol. 10 No. 1, Mar. 2014, 20 printed pages. (Year: 2014).*

Soleyah Groves et al. "Inhaled Cyclosporine and Pulmonary Function in Lung Transplant Recipients." Journal of Aerosol Medicine and Pulmonary Drug Delivery, vol. 23, No. 1, 2010, pp. 31-39. (Year: 2010).*

Juergen Behr et al. "Lung Deposition of a Liposomal Cyclosporine A Inhalation Solution in Patients after Lung Transplantation." Journal of Aerosol Medicine and Pulmonary Drug Delivery, vol. 22 No. 2, 2009, pp. 121-129. (Year: 2009).*

TE Corcoran. "Inhaled delivery of aerosolized cyclosporine." Advanced Drug Delivery Reviews 58 (2006), pp. 1119-1127. (Year: 2006).*

Barik, "Immunophilins: for the love of proteins." *Cell Mol Life Sci.*, vol. 63, No. 24, pp. 2889-2900 (2006).

Behr et al., "Lung Deposition of a Liposomal Cyclosporine A Inhalation Solution in Patients after Lung Transplantation," *Journal of Aerosol Medicine and Pulmonary Drug Delivery*, vol. 22, No. 2, pp. 121-129, 2009.

Corcoran et al., "Inhaled Delivery of Aerosolized Cyclosporine," *Adv Drug Deliv Rev.*, vol. 58, Nos. 9-10, pp. 1119-1127, 2006.

Corcoran et al., "Preservation of Post-Transplant Lung Function with Aerosol Cyclosporin," *Eur Respir J.*, vol. 23, No. 3, pp. 378-383, (2004).

Dalal et al., "Role of Tacrolimus Combination Therapy with Mycophenolate Mofetil in the Prevention of Organ Rejection in Kidney Transplant Patients," *International Journal of Nephrology and Renovascular Disease*, vol. 3, pp. 107-115, (2010).

Estenne et al., "Bronchiolitis Obliterans Syndrome 2001: An Update of the Diagnostic Criteria," *J Hear Lung Transplant*, vol. 21, No. 3, pp. 297-310, (2002).

Groves et al., "Inhaled Cyclosporine and Pulmonary Function in Lung Transplant Recipients," *Journal of Aerosol Medicine and Pulmonary Drug Delivery*, vol. 23, No. 1, pp. 31-39, (2010).

Hachem et al., "Bronchiolitis Obliterans Syndrome: Pathogenesis and Management," *Semin Thorac Cardiovasc Surg.*, vol. 16, No. 4, pp. 350-355, (2004).

Hadjiliadis et al., "Is Transplant Operation Important in Determining Posttransplant Risk of Bronchiolitis Obliterans Syndrome in Lung Transplant Recipients?," *Chest.*, vol. 122, No. 4, pp. 1168-1175, (2002).

Halloran et al., "The 'injury response': A Concept Linking Nonspecific Injury, Acute Rejection, and Long-term Transplant Outcomes," *Transplant Proc.*, vol. 29, Nos. 1-2, pp. 79-81, (1997).

Howard et al., "Electronic Monitoring of Adherence to Inhaled Medication in Asthma," *Current Respiratory Medicine Views*, vol. 10, No. 1, 20 pages, (2014).

Iacono et al., "Dose-related Reversal of Acute Lung Rejection by Aerosolized Cyclosporine," *Am J Respir Crit Care Med.*, vol. 155, No. 5, pp. 1690-1698, (1997).

Iacono et al., "A Randomized Trial of Inhaled Cyclosporine in Lung-Transplant Recipients," *The New England Journal of Medicine*, vol. 354, No. 2, pp. 141-150, (2006).

Iacono A et al: "Stabilization of lung function and survival improvement by aerosolized liposomal cyclosporine a (L-CSA) for bronchiolitis obliterans syndrome", Journal of Heart and Lung Transplantation 20180401 Elsevier USA NLD, vol. 37, No. 4, Supplement 1, Apr. 1, 2018 (Apr. 1, 2018), XP009509346,ISSN: 1557-3117.

International Search Report and Written Opinion mailed May 4, 2016 for Application No. PCT/EP2016/055609.

International Preliminary Report on Patentability dated Sep. 19, 2017 for Application No. PCT/EP2016/055609.

Knoop et al., "Immunosuppressive Therapy After Human Lung Transplantation," *Eur Respir J.*, vol. 23, No. 1, pp. 159-171, (2004).

Kotecha S et al. "Review: immunosuppression for the lung transplant patient." *J. Thorac. Dis.*, 13(11):6628-6644 (2021).

McDermott JK & Girgis RE. "Individualizing immunosuppression in lung transplantation." *Global Cardiology Science and Practice*, 2018:5 (2018).

Moffatt-Bruce et al., "Invited Commentary," *Ann Thorac Surg.*, vol. 88, No. 3, pp. 964-965, (2009); doi: 10.1016/jathoracsur.2009.06.014.

Niven et al., "The Challenges of Developing an Inhaled Cyclosporine Product for Lung Transplant Patients," *Respiratory Drug Delivery*, pp. 51-60, (2012).

Soubani et al., "Bronchiolitis Obliterans Following Haematopoietic Stem Cell Transplantation," *Eur Respir J.*, vol. 29, No. 5, pp. 1007-1019, (2007).

Treede et al., "Tacrolimus and Cyclosporine have Differential Effects on the Development of Bronchiolitis Obliterans Syndrome: Results of a Prospective, Randomized International Trial in Lung Transplantation," *The Journal of Heart and Lung Transplantation*, vol. 31, No. 8, pp. 797-804, (2012).

Weber et al., "Effect of Nebulizer Type and Antibiotic Concentration on Device Performance," *Pediatr Pulmonol.*, vol. 23, No. 4, pp. 249-260, (1997).

Written Opinion of the International Application No. PCT/EP2019/058958, Jul. 11, 2019, 6 pages,.

Iacono, et al., "Aerosol cyclosporin therapy in lung transplant recipients with bronchiolitis obliterans", Eur. Respir. J., vol. 23, 2004, pp. 384-390.

* cited by examiner

Figure 14.2.1.1.1 Kaplan-Meier Curve of BOS-free Survival for SLT Patients
(Full Analysis Set)

Number of Patients at Risk

| | 0 | 4 | 8 | 12 | 16 | 20 | 24 | 28 | 32 | 36 | 40 | 44 | 48 | 52 | 56 | 60 | 64 | 68 | 72 | 76 | 80 | 84 | 88 | 92 | 96 | 100 | 104 | 108 | 112 | 116 | 120 | 124 |
|---|---|---|---|---|---|---|---|---|---|---|---|---|---|---|---|---|---|---|---|---|---|---|---|---|---|---|---|---|---|---|---|---|
| L-CsA | 23 | 20 | 19 | 18 | 18 | 17 | 17 | 16 | 16 | 15 | 15 | 13 | 12 | 11 | 11 | 9 | 9 | 8 | 7 | 7 | 6 | 4 | 4 | 3 | 3 | 1 | 1 | 0 | 0 | 0 | 0 | 0 |
| Placebo | 17 | 16 | 15 | 15 | 14 | 13 | 12 | 12 | 11 | 10 | 9 | 9 | 9 | 9 | 7 | 6 | 5 | 4 | 2 | 2 | 2 | 1 | 1 | 1 | 1 | 0 | 0 | 0 | 0 | 0 | 0 | 0 |

Time (Weeks)

PARI Pharma GmbH: 12011.201/CIL-ELD/FINAL/BOS01XF.SAS
Produced: 7 April 2014, 16:42
Source: Listing 16.2.6.1

Page 1 of 1

Notes: [1] P-value (log-rank test): Active L-CsA vs Placebo: 0.191
[2] SLT = Single Lung Transplant Figure 14.2.1.1.2 Kaplan-Meier Curve of BOS-free Survival for DLT Patients
(Full Analysis Set)

Number of Patients at Risk

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| L-CsA | 51 | 47 | 46 | 44 | 43 | 42 | 41 | 39 | 37 | 35 | 34 | 31 | 30 | 26 | 23 | 22 | 21 | 21 | 19 | 17 | 16 | 15 | 15 | 15 | 12 | 6 | 6 | 1 | 1 | 1 | 0 | 0 |
| Placebo | 39 | 38 | 38 | 34 | 33 | 30 | 30 | 29 | 28 | 27 | 26 | 23 | 23 | 21 | 20 | 19 | 19 | 18 | 17 | 16 | 16 | 15 | 12 | 11 | 9 | 3 | 0 | 0 | 0 | 0 | 0 | 0 |

Time (Weeks)

PARI Pharma GmbH: 12011.201/CIL-ELD/FINAL/BOS01XF.SAS
Produced: 7 April 2014, 16:42
Source: Listing 16.2.6.1

Page 1 of 1

Notes: [1] P-value (log-rank test): Active L-CsA vs Placebo: 0.643
[2] DLT = Double Lung Transplant Figure 14.2.1.2 Kaplan-Meier Curve of BOS-free Survival
(Per Protocol Analysis Set)

Number of Patients at Risk

| | 0 | 4 | 8 | 12 | 16 | 20 | 24 | 28 | 32 | 36 | 40 | 44 | 48 | 52 | 56 | 60 | 64 | 68 | 72 | 76 | 80 | 84 | 88 | 92 | 96 | 100 | 104 | 108 | 112 | 116 | 120 | 124 |
|---|---|---|---|---|---|---|---|---|---|---|---|---|---|---|---|---|---|---|---|---|---|---|---|---|---|---|---|---|---|---|---|---|
| L-CsA | 34 | 34 | 34 | 32 | 32 | 31 | 30 | 29 | 29 | 28 | 27 | 24 | 22 | 20 | 18 | 17 | 16 | 15 | 14 | 12 | 10 | 8 | 8 | 7 | 7 | 2 | 2 | 0 | 0 | 0 | 0 | 0 |
| Placebo | 38 | 37 | 37 | 36 | 34 | 33 | 32 | 31 | 29 | 29 | 27 | 24 | 24 | 23 | 20 | 19 | 19 | 18 | 15 | 15 | 15 | 14 | 12 | 11 | 9 | 3 | 0 | 0 | 0 | 0 | 0 | 0 |

Time (Weeks)

PARI Pharma GmbH: 12011.201/CIL-ELD/FINAL/BOS01XF.SAS
Produced: 7 April 2014, 16:42
Source: Listing 16.2.6.1

Page 1 of 1

Notes: [1] P-value (log-rank test): Active L-CsA vs Placebo: 0.212

Figure 14.2.1.2.2 Kaplan-Meier Curve of BOS-free Survival for DLT Patients
(Per Protocol Analysis Set)

Number of Patients at Risk

L-CsA 22 22 22 20 20 19 18 18 18 17 16 15 14 12 10 10 9 9 9 7 6 5 5 5 5 1 1 0 0 0 0 0
Placebo 26 25 25 24 23 22 22 21 20 20 19 16 16 15 14 14 14 14 13 13 13 13 11 10 8 3 0 0 0 0 0 0

Time (Weeks)

PARI Pharma GmbH: 12011.201/CIL-ELD/FINAL/BOS01XF.SAS
Produced: 7 April 2014, 16:42
Source: Listing 16.2.6.1

Page 1 of 1

Notes: [1] P-value (log-rank test): Active L-CsA vs Placebo: 0.973
[2] DLT = Double Lung Transplant Figure 14.2.3.3 Changes from maximum value of FEV1 (L) by assessment point
(Full Analysis Set)

PARI Pharma GmbH: 12011.201/CIL-ELD/FINAL/FEV03XF.SAS
Produced: 10 April 2014, 18:22
Source: Listing 16.2.6.2
Notes: [1] SE = Standard Error
[2] Maximum (best) value is defined as the patient's maximum (best) value achieved in any former assessment Page 1 of 1

Figure 14.2.3.4 Changes from maximum value of FEV1 (L) by assessment point
(Per Protocol Analysis Set)

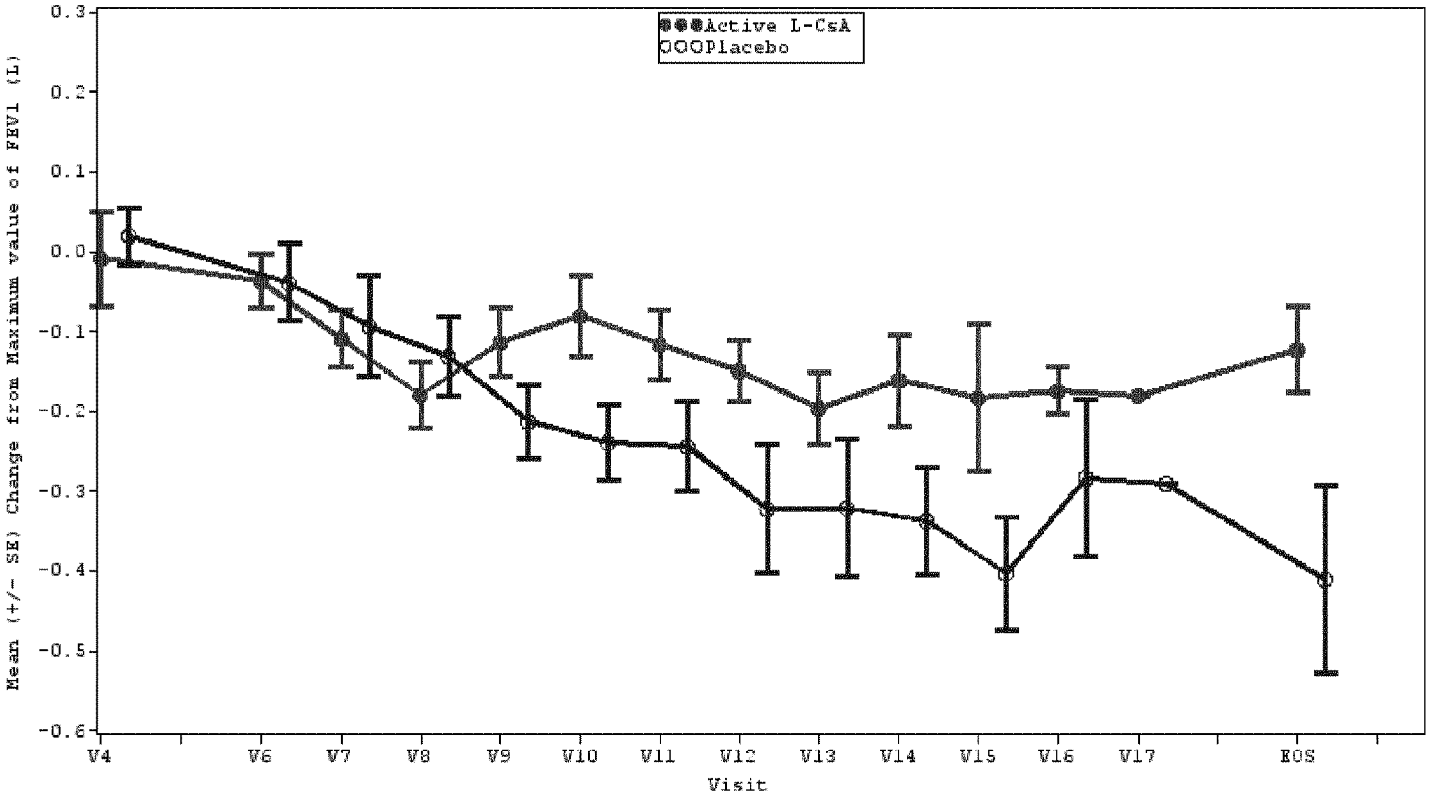

| | V4 | V6 | V7 | V8 | V9 | V10 | V11 | V12 | V13 | V14 | V15 | V16 | V17 | EOS |
|---|---|---|---|---|---|---|---|---|---|---|---|---|---|---|
| N= | 30 37 | 31 32 | 28 32 | 30 31 | 28 29 | 23 27 | 21 20 | 16 17 | 12 17 | 9 15 | 7 12 | 7 13 | 1 1 | 19 18 |
| p-value= | 0.673 | 0.974 | 0.843 | 0.464 | 0.124 | 0.026 | 0.081 | 0.068 | 0.262 | 0.083 | 0.074 | 0.440 | | 0.030 |

PARI Pharma GmbH: 12011.201/CIL-ELD/FINAL/FEV03XF.SAS
Produced: 10 April 2014, 18:22
Source: Listing 16.2.6.2
Notes: [1] SE = Standard Error
[2] Maximum (best) value is defined as the patient's maximum (best) value achieved in any former assessment
[3] p-value tests the equality of means at each visit Page 1 of 1

Figure 12

Figure 14.2.3.4.1 Changes from maximum value of FEV1 (L) by assessment point for SLT Patients
(Per Protocol Analysis Set)

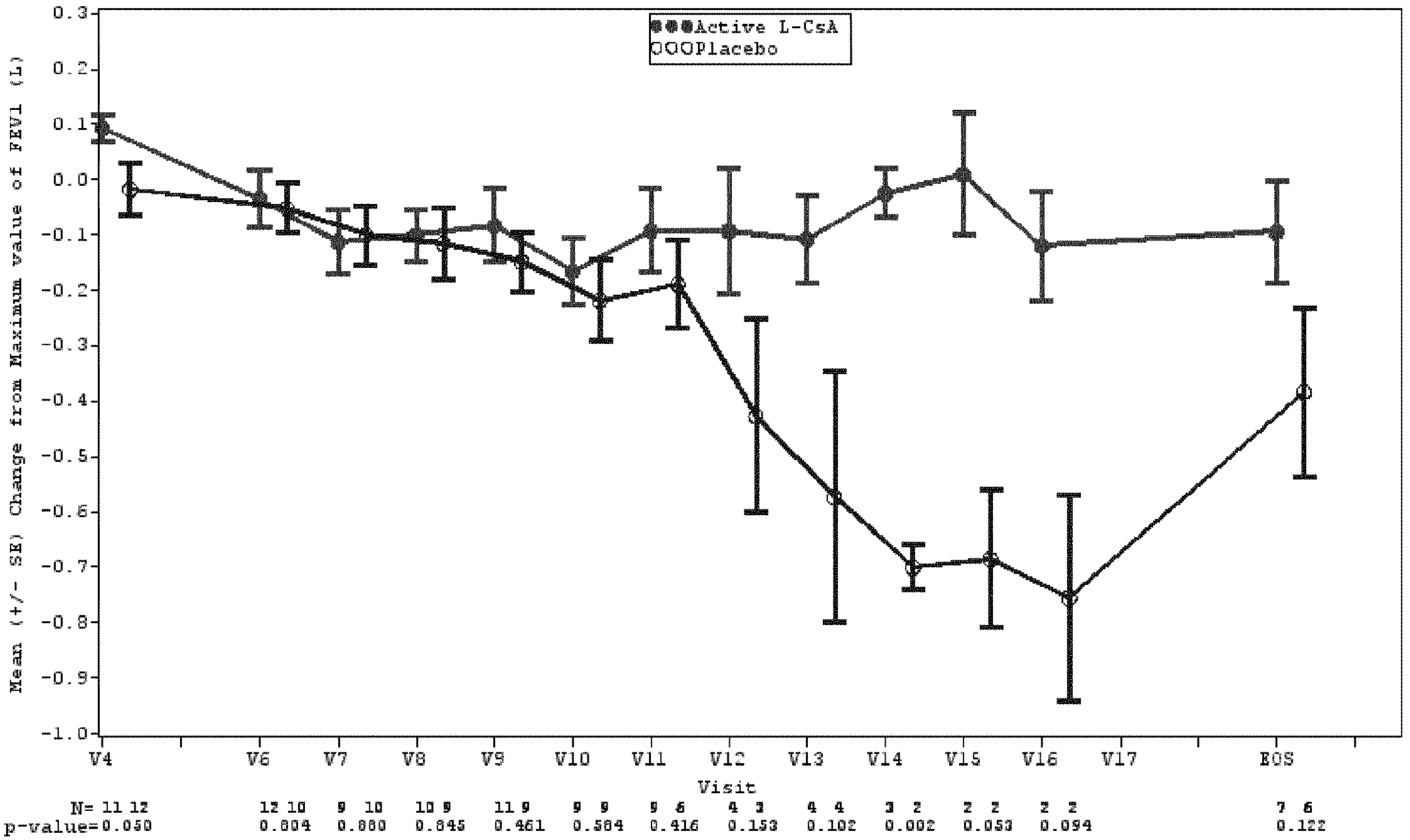

PARI Pharma GmbH: 12011.201/CIL-ELD/FINAL/FEV03XF.SAS
Produced: 10 April 2014, 18:22 Page 1 of 1
Source: Listing 16.2.6.2
Notes: [1] SE = Standard Error
[2] Maximum (best) value is defined as the patient's maximum (best) value achieved in any former assessment
[3] SLT = Single Lung Transplant
[4] p-value tests the equality of means at each visit

Figure 13

Figure 14.2.3.4.2 Changes from maximum value of FEV1 (L) by assessment point for DLT Patients
(Per Protocol Analysis Set)

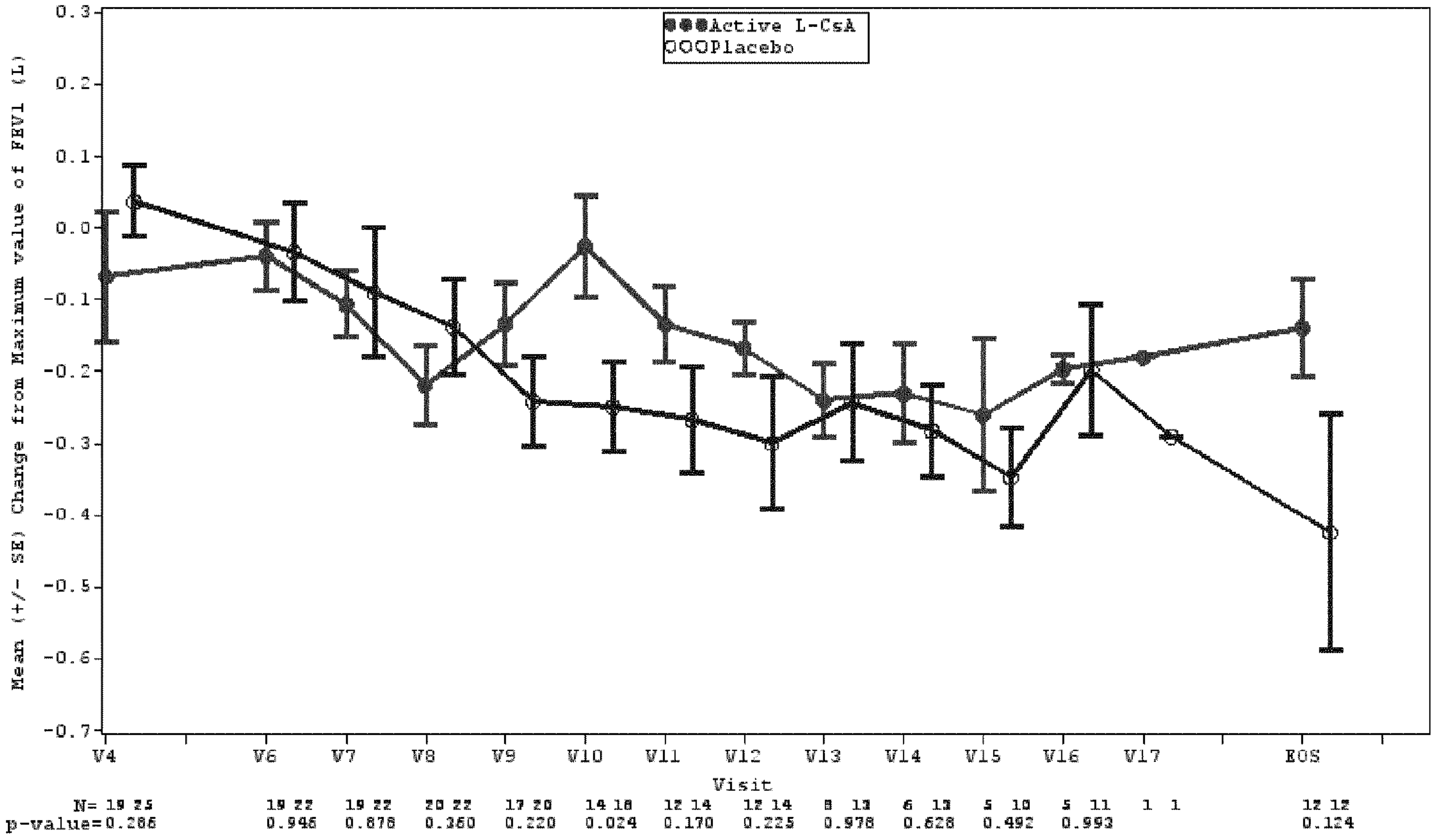

PARI Pharma GmbH: 12011.201/CIL-ELD/FINAL/FEV03XF.SAS
Produced: 10 April 2014, 18:22 Page 1 of 1
Source: Listing 16.2.6.2
Notes: [1] SE = Standard Error
[2] Maximum (best) value is defined as the patient's maximum (best) value achieved in any former assessment
[3] DLT = Double Lung Transplant
[4] p-value tests the equality of means at each visit

Figure 14

CYCLOSPORINE FORMULATIONS FOR USE IN THE PREVENTION OR TREATMENT OF PULMONARY CHRONIC GRAFT REJECTION

CROSS-REFERENCE TO RELATED APPLICATIONS

This application is a continuation of U.S. application Ser. No. 17/086,254, filed on Oct. 30, 2020, which is a continuation of U.S. application Ser. No. 15/558,102, filed on Sep. 13, 2017, which is a U.S. National Stage application under 35 U.S.C. § 371 of International Application No. PCT/EP2016/055609, filed on Mar. 15, 2016, which claims priority to and the benefit of European Application No. 15020035.0, filed on Mar. 16, 2015, the contents of each of which are hereby incorporated by reference in their entireties.

FIELD OF THE INVENTION

The invention relates to cyclosporine liquid formulations for use in a method of preventing or treating pulmonary chronic graft rejection after lung transplantation.

BACKGROUND OF THE INVENTION

Lung transplantation has become an effective treatment option for a variety of chronic and end-stage lung diseases. Lung preservation techniques have been developed over time resulting in satisfactory short-term results (Hachem R R, Trulock E P. Bronchiolitis obliterans syndrome: pathogenesis and management. *Semin Thorac Cardiovasc Surg* 2004; 16:350-355). Immunosuppression is a key post-transplant intervention usually consisting of a triple therapy regimen, including systemic cyclosporine A (CsA) or tacrolimus, azathioprine or mycophenolate mofetil and corticosteroids (Knoop C, et al. Immunosuppressive therapy after human lung transplantation. *Eur Respir J* 2004; 23:159-171).

Both the transplantation of a single lung as well as the transplantation of both lungs is possible. Single lung transplantation is indicated, for example, in the case of certain forms of emphysema and fibrosis, such as idiopathic pulmonary fibrosis, and/or chronic obstructive pulmonary disease (COPD). Double lung transplantation is indicated in cases of cystic fibrosis, primary pulmonary hypertension, alpha-1-antitrypsin deficiency, emphysema with global insufficiency, frequent serious infections as well as idiopathic pulmonary fibrosis with complication by repeated infections.

Despite systemic immunosuppressive therapy with cyclosporine or tacrolimus, azathioprine or mycophenolate mofetil and corticosteroids, chronic rejection after lung transplantation is a severe pulmonary complication accounting for 30% of deaths in lung transplantation, thus making the evaluation for new therapeutic options desirable.

Development of bronchiolitis obliterans (BO), a major contributor to pulmonary chronic graft dysfunction, is the leading cause of morbidity and mortality in long-term survivors of lung transplantation and remains the major limitation to long-term survival after lung transplantation. It occurs in 60-70% of transplant recipients who survive five years. The median time to development of BO is approximately 18 months. Although the pathogenesis of BO is multifactorial and is not completely understood, chronic rejection resulting from immune-dependent responses (acute rejection episodes) is considered to be the predominant cause of BO (Moffatt-Bruce S., "Invited commentary", Ann Thorac Surg. 2009 September; 88(3):964-5. doi: 10.1016/j.athoracsur.2009.06.014) after lung transplantation despite the use of systemic calcineurin inhibitors for immunosuppression (Iacono A T, et al. A randomized trial of inhaled cyclosporine in lung-transplant recipients. *N Engl J Med* 2006; 354:141-150). Once chronic rejection develops, airway damage is progressive and irreversible and patients eventually die of graft failure or pneumonia.

Currently, satisfactory therapeutic options for the prevention or treatment of BO syndrome (BOS) following lung transplantation are not available. Augmented immunosuppression using higher doses of commonly used drugs for basic immunosuppression have been proven ineffective and are contemporarily associated with a higher adverse event rate over time due to the increased drug burden. Immunosuppressive antibodies may be useful for the prevention of acute pulmonary graft rejection but therapeutic attempts to treat chronic rejection have produced disappointing results. From the pathomechanistic point of view this is comprehensive because acute lung graft rejection is basically a vasculitis starting with deleterious reactions on the epithelium of blood vessels. In contrast, although still not completely understood in all details, there is consent that the origin of chronic lung rejection resides in the lung lumen, i.e. the bronchioli, and therefore is rather a bronchiolitis than a vasculitis. Systemically administered drugs thus are challenged to cross the capillary-alveolar barrier. Photopheresis is frequently selected as a last resort measure in high-stage BOS patients and performed rather for psychological purposes than for medical reasons. Thus, new therapies for the prevention and treatment of pulmonary chronic graft rejection are highly desired.

From the early experimental lung transplantations onwards it became clear that the outcome of double lung transplantation was superior to that of single lung transplantation. This experience turned out to become unique even in times when lung transplantation techniques were refined and became established as a routine intervention to rescue patients with end-stage pulmonary diseases. Even with improvements in medical supply and post-transplant patient care the results after single lung transplantation are still not satisfactory. Currently, the median survival is 4.6 years in single lung transplanted patients, whereas it is 6.6 years in double lung transplanted patients. It has been shown that this different survival is related to a considerable delay in the onset of BOS after double lung transplantation compared to single lung transplantation (Hadjiliadis D, et al. Is transplant operation important in determining posttransplant risk of bronchiolitis obliterans syndrome in lung transplant recipients? *Chest* 2002; 122:1168-1175).

The superior overall outcome of double lung transplantations caused a general shift over time from single to double lung transplantations whenever possible. However, apart from indications such as cystic fibrosis and idiopathic pulmonary arterial hypertension for which it was recognized early that double lung transplantation was medically required, single lung transplantation would be sufficient for other indications. In particular, patients suffering from chronic obstructive pulmonary disease and idiopathic pulmonary fibrosis are frequently of higher age. Often, age-related co-morbidities are present and the patients suffer more from the traumatic burden associated with the surgical procedure of double lung transplantation. Thus, an improvement of the outcome of single lung transplantation is particularly desired.

Successful prevention of BO is identified as a major requirement to improve the outcome of lung transplantation.

It has been suggested that the most important cause of BO is T-lymphocyte activation by major histocompatibility antigen- or immune-dependent mechanisms (Soubani A O, Uberti J P. Bronchiolitis obliterans following haematopoietic stem cell transplantation. *Eur Respir J* 2007; 29:1007-1019; Halloran P F, et al. The "injury response": A concept linking nonspecific injury, acute rejection, and long-term outcomes. *Transplant Proc* 1997; 29:79-81). From systemic application, it is well known that CsA blocks T-lymphocyte proliferation by inhibiting the phosphatase activity of calcineurin enzyme and reduces the expression of several cytokines genes (e.g. for interleukin [IL]-2) that are normally induced on T-cell activation.

While most solid organ transplants are inaccessible to localized immunotherapy, lung transplants are the exception due to their unique communication with the external environment making inhalation a therapeutic option.

It has been proposed that a topical application of CsA to the lungs may improve efficacy with the potential to reduce systemic exposure of toxic immunosuppressants (Iacono A, et al. Dose related reversal of acute lung rejection by aerosolized ciclosporin. *Am J Respir Crit Care Med* 1997; 155:1690-1698). Cyclosporine A is a cyclic polypeptide consisting of 11 amino acids. It is produced as a metabolite by the fungus species *Beauveria nivea*. Cyclosporine is an immunosuppressant belonging to the group of calcineurin inhibitors which has been used to prevent graft rejection after organ transplantation in most of the post-transplant regimens since the early 1980s in Europe.

From the study of Corcoran et al. (Preservation of post-transplant lung function with aerosol cyclosporin. *Eur Respir J* 2004; 23:378-383) it has been concluded that a CsA propylene glycol (CsA-PG) peripheral lung deposition of approximately 5 mg or higher would improve lung function of transplant patients whereas lower doses resulted in a decline. From the latter study, it was derived that an effective threshold of 15 mg/week or 2 mg/day CsA deposited in the periphery of the lung(s) should be achieved for a therapeutic effect.

A phase II clinical trial with 58 lung transplanted patients showed after up to two years treatment with inhaled CsA-PG a statistical significant difference in BO-free survival and overall survival in favour of CsA-PG therapy versus placebo (Iacono A T, et al. A randomized trial of inhaled cyclosporine in lung-transplant recipients. N Engl *J Med* 2006; 354:141-150). In contrast, a multi-centre phase III clinical trial showed no efficacy beyond that of standard of care when CsA was used as supplemental targeted therapy to prevent chronic rejection in lung transplant patients. The outcome of this study is at odds with numerous preclinical and clinical studies which allow for expectation of a therapeutic response. From this result, it was concluded that administering a cyclosporine aerosol to this highly vulnerable patient population is not without challenges and that one or more of these challenges may have influenced the study outcome. It was concluded from an analysis of these challenges that the use of a more convenient delivery system administering drug at more frequent intervals within a setting of inhalation treatment or systemic replacement may prove successful (Niven R W, et al. The challenges of developing an inhaled cyclosporine product for lung transplant patients. *Respiratory Drug Delivery* 2012; 51-60).

With respect to the CsA-PG formulation, patient intolerance and lack of adherence due to the long inhalation time of up to 30 min have been reported (Corcoran T E. Inhaled delivery of aerosolized cyclosporine. *Adv Drug Deliv Rev* 2006; 58:1119-1127). Propylene glycol is known to be hyperosmotic with potential to be intolerable by the patients thus requiring pre-medication with a bronchodilator and local anaesthetic drug.

In view of these issues, a new liposomal formulation of cyclosporine for inhalation use was developed. The formulation is described in WO 2007/065588.

Furthermore, new inhalation systems have been proposed for the inhalation of CsA, which are supposed to allow a more efficient deposition of CsA in the lungs. Examples of such systems are vibrating membrane nebulizers. Such inhalation systems achieve a better targeting of the drug by production of particles with the appropriate size for high peripheral deposition. Also, the high drug delivery rate of such devices supports much shorter inhalation times which are expected to be advantageous with respect to patient adherence.

In a Phase Ib clinical trial the lung deposition and pharmacokinetics of 10 and 20 mg radio-labelled aerosolized liposomal CsA (L-CsA) were investigated in five double lung transplanted patients and seven single lung transplanted patients. The aerosol was generated with an eFlow® nebulizer. Patients were given a single dose application of 10 or 20 mg of liposomal CsA, which was well tolerated. It was shown that 40±6% (for the 10 mg dose) and 33±7% (for the 20 mg dose), respectively, was deposited in the lung. This resulted in a peripheral lung dose of 2.2±0.5 mg (for the mg dose) and 3.5±0.9 mg (for the 20 mg dose), respectively. Assuming single or twice daily dosing with 10 mg nominal drug amount of L-CsA, 14 and 28 mg/week peripheral deposition could be achieved, respectively. Overall inhalation time for the and 20 mg nominal dose was approximately 9±1 min and 20±5 min, respectively. In single lung transplanted patients, almost the entire deposition (88-90%) occurred in the transplanted part of the lung. There were no statistically significant differences between patients with single and double lung transplantation.

Although several preclinical and clinical studies have been performed with inhaled CsA, the conclusions with respect to the actual efficacy of inhaled cyclosporine are contradicting. Thus, available studies do not allow any conclusion with respect to the actual efficacy of inhaled liposomal cyclosporine to prevent or treat pulmonary chronic graft rejection after lung transplantation.

SUMMARY OF THE INVENTION

The invention provides a cyclosporine liquid formulation for use as an aerosol for inhalation in a method of preventing or treating pulmonary chronic graft rejection in single lung transplanted patients. Preferably, the formulation is a liposomal formulation.

In a preferred embodiment, the formulation is administered once or twice daily.

It is preferred that the formulation contains the cyclosporine at a concentration of 1 up to 5 mg/ml. The volume of a unit dose of the formulation is preferably less than 10 ml and more preferably from 1 to 3 ml.

In a particular embodiment, the formulation is aerosolized with an electronic vibrating membrane nebulizer. The nebulizer can comprise features for monitoring for example the time, date and duration of inhalation by the patient. Preferably, the formulation is inhaled as intended in at least 65% of the intended inhalation cycles. More preferably, the formulation is inhaled as intended in at least 75% of the intended inhalation cycles. In this respect, the time, date and duration of inhalation by the patient can be monitored. If the inhalation of the formulation is not carried out or not finished as defined, the monitor system can produce a signal indicating an insufficient patient adherence.

In a further embodiment, the formulation is used in combination with one or more active ingredients used in standard immunosuppressive therapy after lung transplantation. Preferably, the dose of the one or more active ingredients used in combination with the formulation is lower than the dose used in standard immunosuppressive therapy after lung transplantation. The one or more active ingredients used in combination with the formulation are preferably selected from the group consisting of tacrolimus, mycophenolate mofetil and corticosteroids.

According to a particular embodiment, the pulmonary chronic graft rejection is characterized by bronchiolitis obliterans syndrome (BOS). In another aspect, the pulmonary chronic graft rejection is characterized by a reduction of the forced expiratory volume in one second ($FEV_1$) of at least 20% from the patient's maximum values, for example confirmed by two separate measurements, which are preferably at least three weeks apart (Estenne M, et al. Bronchiolitis obliterans syndrome 2001: an update of the diagnostic criteria. *J Heart Lung Transplant.* 2002; 21 (3): 297-310)

Finally, the formulation is preferably used in single lung transplanted patients who suffered from emphysema and fibrosis, such as idiopathic pulmonary fibrosis, and/or chronic obstructive pulmonary disease (COPD) before the lung transplantation.

BRIEF DESCRIPTION OF THE DRAWINGS

FIG. 12: Changes from maximum value of $FEV_1$ (L) by assessment point for all patients (per protocol analysis set)

FIG. 13: Changes from maximum value of $FEV_1$ (L) by assessment point for single lung transplanted patients (per protocol analysis set)

FIG. 14: Changes from maximum value of $FEV_1$ (L) by assessment point for double lung transplanted patients (per protocol analysis set)

DETAILED DESCRIPTION OF THE INVENTION

Figure 1:
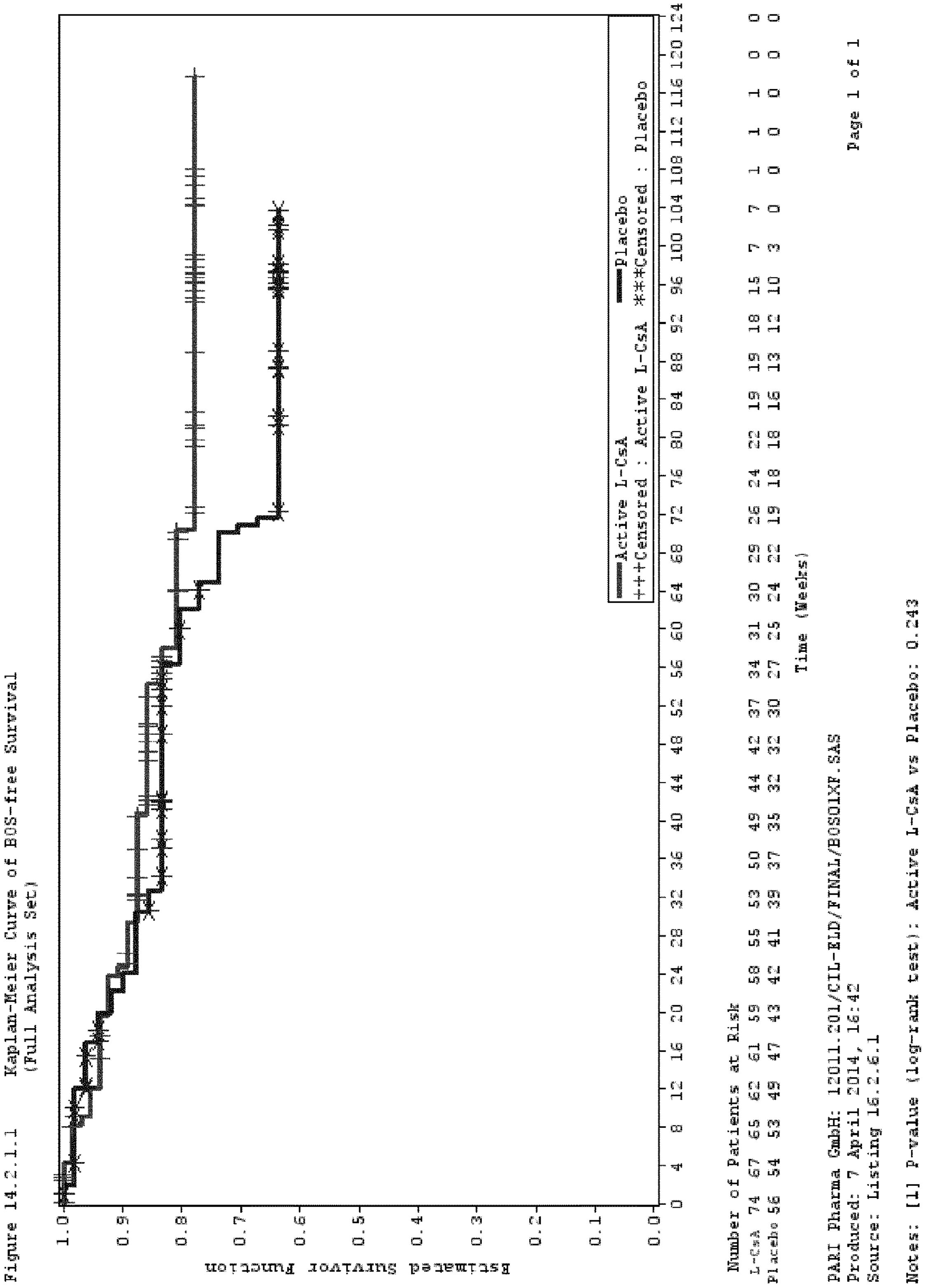
FIG. 1: Kaplan-Meier curve of BOS-free survival for all patients (full analysis set)

Cyclosporine liquid formulations that can be used in the invention have been described in detail in WO 2007/065588. In summary, these formulations comprise a therapeutically effective dose of a cyclosporine, an aqueous carrier liquid, a first solubility enhancing substance selected from the group of phospholipids and a second solubility enhancing substance selected from the group of non-ionic surfactants.

Preferably, the phospholipid is a mixture of natural phospholipids, such as lecithins. Examples of commercially available lecithins are Lipoid S 100 or Phospholipon G90. Among the non-ionic surfactants, polysorbates, tyloxapol, and vitamin E-TPGS are preferred, especially polysorbate 80. These formulations are free of irritant organic solvents such as propylene glycol.

Preferably, the formulation is a liposomal formulation. The liposomes which are formed primarily by the phospholipids contained in the composition are preferably unilamellar liposomes. The liposomes preferably have an average diameter of at most about 100 nm measured as z-average using photon correlation spectroscopy with for example a Malvern ZetaSizer device, and a polydispersity index of at most about 0.5, preferably at most about 0.4 also measured by photon correlation spectroscopy.

The formulation can be presented as a solid formulation for reconstitution with an aqueous solvent immediately before inhalation. The solid formulation can be prepared by any method suitable for removing the solvent from a liquid formulation. Preferred examples of methods for preparing such solid formulation are freeze drying and spray drying. Preferably, freeze drying is used.

To protect the active ingredient during the drying process, it may be useful to incorporate lyoprotective and/or bulking agents, such as a sugar or a sugar alcohol, in particular sucrose, fructose, glucose, trehalose, mannitol, sorbitol, isomalt, or xylitol. Of these agents, sucrose is particularly preferred.

The portion of the solid composition comprising an effective amount of the active compound (i.e. a unit dose) is preferably dissolvable or dispersible in an aqueous solvent having a volume of not more than about 10 ml. Preferably, it is dissolvable or dispersible in an aqueous liquid volume of not more than about 5 ml, not more than about 4 ml, or even not more than about 3 ml. The volume of the solution required for reconstitution will depend on the dose of the active ingredient, as well as on the desired concentration. If a smaller dose is required for a therapeutic effect, a smaller volume might be sufficient to dissolve or disperse the solid composition.

An aqueous solution is preferably used for reconstitution. Preferably, a saline solution is used, wherein the concentration of sodium chloride is adjusted in order to yield a liquid formulation which has a physiologically acceptable osmolality and tolerability after reconstitution. The osmolality of physiological fluids is about 290 mOsmol/kg. A certain degree of hypo- and hyper-osmolality is generally still tolerated. The presence of permeant anions (such as chloride) in a concentration between 31 and 300 mM improves tolerability (Weber et al. "Effect of nebuliser type and antibiotic concentration on device performance", Paediatric Pulmonology 23 (1997) 249-260). A hyperosmotic formulation can actually be preferred in certain applications. For example, the osmolality of the reconstituted formulation may range between 150 and 800 mOsmol/kg. Preferably, the formulation has an osmolality of about 250 to about 700 mOsmol/kg, or of about 250 to 600 mOsmol/kg. Most preferred, the formulation has an osmolality of about 400 to about 550 mOsmol/kg.

Depending on the osmolality of the formulation before drying, the concentration of sodium chloride can range between 0.1 and 0.9% (w/v). Preferably, a 0.25% (w/v) saline solution is used.

The solid composition for reconstitution may be part of a pharmaceutical kit. Such kit preferably comprises the solid composition together with the aqueous solution for reconstitution. Such a kit for preparation of liquid composition for administration as an aerosol is described in WO 03/035030.

After reconstitution, the formulation should have the same composition as before drying. In case the formulation is a liposomal formulation, it should also contain liposomes after reconstitution. Preferably, also the size of the liposomes is similar before drying and after reconstitution. With respect to the size of the liposomes, it is particularly preferred that the liposomes' size measured as z-average by photon correlation spectroscopy is between 40 and 100 nm, exhibiting a uniform size distribution (polydispersity index<0.4) after reconstitution with 0.25% saline.

The inventors have now found that the use of a cyclosporine liquid formulation in the prevention or treatment of pulmonary chronic graft rejection is particularly advantageous in single lung transplanted patients. More specifically, a considerable delay in the onset of pulmonary chronic graft rejection can be obtained in patients who inhale a cyclosporine liquid formulation instead of a placebo formulation in addition to standard immunosuppressive therapy. A comparable delay was not found within the same timeframe in a double lung transplanted population.

The different effect of the inhaled cyclosporine formulation in view of the type of transplantation was not expected. Actually, to be able to treat both single and double lung transplanted patients as one population, the dose administered to single lung transplanted patients was half of the dose administered to double lung transplanted patients. Since cyclosporine has a topical effect, it was expected that the same effect would be obtained with a dose reduced by half where the target surface was also reduced by half. In other words, it was expected that the same effect would be obtained in single and double lung transplanted patients when the dose was adjusted depending on the type of transplantation. Nevertheless, even when administering a comparable dose, the inventors found that the effect of inhaled cyclosporine in the prevention of pulmonary chronic graft rejection was much more pronounced in the single lung transplanted population.

It was found that the use of inhaled cyclosporine may increase the outcome after single lung transplantation to the level achieved after double lung transplantation. Therefore, an inhaled cyclosporine formulation used in single lung transplanted patients may contribute to counteract the general shortage of donor organs in indications which do not necessarily require double lung transplantation for medical reasons.

The formulation of the invention can be administered according to a pre-determined dosing regimen. Especially, the formulation can be administered a specific number of times during each week of treatment. For example, the formulation can be administered three times per week. Preferably, the formulation is administered daily. Even more preferred, the formulation is administered twice daily.

The formulation preferably contains cyclosporine at a concentration between about and 10 mg/ml, preferably between about 1 and 6 mg/ml, and more preferably of 1 up to 5 mg/ml. Most preferred, the formulation contains cyclosporine at a concentration of about 4 mg/ml.

The volume of a unit dose is preferably low in order to allow short nebulization times. The volume, also referred to as the volume of a dose, or a dose unit volume, or a unit dose volume, should be understood as the volume which is intended for being used for one single administration. A unit dose is defined as the dose of cyclosporine in the formulation filled in the nebulizer for one single administration. Specifically, the volume of a unit dose may be less than 10 ml. Preferably, the volume is in the range from about 0.3 to about 3.5 ml, more preferably about 1 to about 3 ml. For example, the volume is about 1.25 ml or about 2.5 ml. In case the formulation is obtained after reconstitution, the volume of the saline solution for reconstitution should be adapted according to the desired volume of the reconstituted formulation.

The unit dose preferably ranges between 1 mg and 15 mg. Most preferred, a unit dose of about 5 mg is applied in single lung transplanted patients. About 10 mg cyclosporine can be applied in double lung transplanted patients. Such doses were found to be well tolerated by lung transplanted patients.

The daily dose of cyclosporine can range between 2 mg and 30 mg. In a preferred embodiment, a daily dose of about 10 mg cyclosporine is administered to single lung transplanted patients. About 20 mg cyclosporine can be administered to double lung transplanted patients.

The nebulizer used according to the invention must be able to convert a solution, colloidal formulation or suspension into a high fraction of droplets which are able to reach the periphery of the lungs. Preferably, a jet nebulizer, ultrasonic nebulizer, piezoelectric nebulizer, electro-hydrodynamic nebulizer, membrane nebulizer, electronic membrane nebulizer, or electronic vibrating membrane nebulizer is used. Examples of suitable nebulizers include the SideStream® (Philips), AeroEclipse® (Trudell), LC Plus® (PARI), LC Star® (PARI), LC Sprint® (PARI), 1-Neb® (Philips/Respironics), IH50 (Beurer), MicroMesh® (Health & Life, Schill), Micro Air® U22 (Omron), Multisonic® (Schill), Respimat® (Boehringer), eFlow® (PARI), AeroNeb Go® (Aerogen), AeroNeb Pro® (Aerogen), and AeroDose® (Aerogen) device families.

A particularly preferred nebulizer for targeting the drug to the lower respiratory tract is an electronic vibrating membrane nebulizer, especially the eFlow® electronic vibrating membrane nebulizer (PARI Pharma GmbH).

The eFlow® nebulizes liquid drug formulations with a perforated vibrating membrane resulting in an aerosol with a low ballistic momentum and a high percentage of droplets in a respirable size range, usually below 5 μm. The eFlow® is designed for a more rapid and efficient nebulization of medication due to a higher nebulization rate, lower drug wastage and a higher percentage of drug available as delivered dose (DD) and respirable dose (RD) compared to conventional jet nebulizers.

Preferably, the nebulizer can deliver such a unit dose at a rate of at least about 0.1 ml/min or, assuming that the relative density of the composition will normally be around 1, at a rate of at least about 100 mg/min. More preferably, the nebulizer is capable of generating an output rate of at least about 0.15 ml/min or 150 mg/min, respectively. In further embodiments, the output rates of the nebulizer are at least about 0.2, 0.3, 0.4, 0.5, 0.6, 0.7, 0.8, 0.9 or 1 nil/min.

Furthermore, the output rate of the nebulizer should be selected to achieve a short nebulization time of the liquid composition. Obviously, the nebulization time will depend on the volume of the composition which is to be aerosolized and on the output rate. Preferably, the nebulizer should be selected or adapted to be capable of aerosolizing a volume of the liquid composition comprising an effective dose of the active compound within not more than about 20 minutes. More preferably, the nebulization time for a unit dose is not more than about 10 minutes. Even more preferred, the nebulization time for a unit dose is not more than about 5 min.

In addition to providing a high delivered dose and having short nebulization times, the nebulizer for administering cyclosporine is preferably constructed in such way that contamination of the environment with cyclosporine is inhibited. For this purpose, a filter device can be placed on the exhalation valve of the nebulizer.

In a preferred embodiment, the nebulizer comprises features for monitoring for example the time, date and duration of inhalation by the patient. An example of such features is a chip card on which the nebulization time and duration are recorded.

Alternatively, wireless transmission of such data to a cloud and/or server can be applied. This enables medical staff to check patient adherence. The monitoring system may comprise a nebulizer, controller, server, databank, cloud, provider, physician, health insurance company and/or telephone service.

It has been found by the inventors that an adherence of at least 65% is required for obtaining a relevant improvement with respect to the prevention of pulmonary chronic graft rejection. To reach an adherence of at least 65%, the patient must inhale the formulation as intended in at least 65% of the intended inhalation cycles. With a twice daily inhalation regimen, this means that the patient is not allowed to miss more than 39 inhalations in a period of 8 weeks, which is equivalent to approximately 5 inhalations per week. Any inhalation that is omitted, that is not performed until the complete unit dose is inhaled or that is deficient for any other reason is considered to be a "missed" inhalation, or in other words an inhalation which is not "as intended". More preferably, the formulation is inhaled with an adherence of at least 75%, i.e. the patient must inhale the formulation as intended in at least 75% of the intended inhalation cycles. This is reached when no more than 28 inhalations are missed in a period of 8 weeks, or approximately 3.5 inhalations per week.

In another embodiment, the features for recording the nebulization time, date and duration are connected with a system which generates a signal as soon as the inhalation is not performed timely and correctly in a predetermined number of inhalation cycles. Due to the use of such monitoring systems, either without or with systems generating a signal, it can be assured that patients use the nebulizer device correctly. The system for generating the signal may include, for example, detection by a sensor of, for example, the presence of a fluid in the fluid reservoir, the measurement of the inhalation flow, inhalation time, inhalation duration, and/or inhalation volume. Visual, audible or sensory feedback can be given, for example, on the relevant patient behaviour and use factors affecting therapy or on the diagnosis of the application. This feedback may include information to improve the patient adherence to a defined medical treatment protocol and/or the drug deposition and distribution in the lungs.

In embodiments where for example the time, date and duration of each inhalation is recorded on features for monitoring, it is possible to continuously monitor the patient. In the embodiment where the monitoring system is connected with a system generating a signal, the inhalation behaviour of the patient can be corrected as soon as the adherence of the patient decreases below a predefined adherence limit. The signal can be a signal generated by the nebulizer itself, but can also be a signal generated on a remote device, which e.g. notifies the patient's medical practitioner. Upon being notified of the lack of adherence, the medical practitioner can contact the patient in order to remind the patient that proper inhalation is a prerequisite for a successful prevention of pulmonary chronic graft rejection.

The inventors have found that monitoring is useful in lung transplanted patients, and especially in single lung transplanted patients, since the effect of a cyclosporine liquid inhaled formulation is more pronounced in compliant patients.

In a further embodiment, the inhaled cyclosporine formulation is used in combination with one or more active ingredients used in standard immunosuppressive therapy after lung transplantation.

In immunosuppressive therapy after lung transplantation one or more active ingredients of the groups of immunosuppressants and corticosteroids can be administered. Examples of immunosuppressants are compounds belonging to the groups of immunoglobulins (antibodies), cell-cycle inhibitors (anti-metabolites/anti-proliferatives), such as azathioprine and mycophenolic acid and its salts, and calcineurin inhibitors, such as cyclosporine, tacrolimus, or mTOR inhibitors such as sirolimus and everolimus. Examples of corticosteroids are compounds belonging to the group of hydrocortisone, methylprednisolone, prednisone, and any of their salts, esters and derivatives.

Preferably, the formulation for inhalation according to the invention is used in combination with one or more active ingredients selected from the group consisting of tacrolimus, mycophenolate mofetil and/or corticosteroids in an oral standard immunosuppressive therapy. Most preferred, the formulation is used in combination with a triple drug therapy, where a combination of a calcineurin inhibitor, a cell-cycle inhibitor and a corticosteroid is administered. Preferably, the calcineurin inhibitor is tacrolimus, the cell-cycle inhibitor is mycophenolate mofetil and the corticosteroid is prednisone. The active ingredients used in combination with the formulation according to the invention are preferably administered orally.

A reasonable consequence is that the usual dose of active ingredients used in standard immunosuppressive therapy can be reduced when a cyclosporine liquid formulation for inhalation is used in combination with these ingredients. In other words, the dose which is generally required for successful immunosuppression when not using inhaled cyclosporine—which is herein defined as the usual dose—can be reduced. This is advantageous since the use of systemically administered immunosuppressants can lead to considerable adverse effects, which are generally dose dependent.

In a particular embodiment, the pulmonary chronic graft rejection is characterized by bronchiolitis obliterans syndrome (BOS). The existence of BO can be determined on the basis of spirometric measurements of the forced expiratory volume. Preferably, the reduction of the forced expiratory volume in one second ($FEV_1$) is used as an indicator of the existence of BO and the risk of pulmonary chronic graft rejection. $FEV_1$ measurements can be performed according to current American Thoracic Society (ATS)/European Respiratory Society (ERS) spirometry guidelines. The forced expiratory volume in one second is expressed in litre.

BOS is considered to exist when a sustained decrease in $FEV_1$ of at least 20% from the patient's maximum values in the absence of other causes occurs and when this is confirmed on the basis of histological markers for BO. BOS may be confirmed by at least two $FEV_1$ measurements which are at least three weeks apart. Maximal post-transplant values are the two best $FEV_1$ values taken at least three weeks apart. $FEV_1$ measurements must be sustained and measured at least three weeks apart. Bronchodilators must be stopped prior to assessing $FEV_1$. It is assumed that decreases in $FEV_1$ due to causes other than chronic rejection such as acute rejection or lymphocytic bronchitis or infection will respond to appropriate medical management and that sustained irreversible declines in function are related to progression of chronic rejection and BOS.

Based on the percentage of decrease of $FEV_1$, BOS grading is possible (Estenne M, et al. Bronchiolitis obliterans syndrome 2001: an update of the diagnostic criteria. *J Heart Lung Transplant* 2002; 21(3): 297-310). The following definitions and criteria can be applied:

BOS 0: $FEV_1$>90% of baseline

BOS 0-p: $FEV_1$ 81% to 90% of baseline

BOS 1: $FEV_1$ 66% to 80% of baseline

BOS 2: $FEV_1$ 51% to 65% of baseline

BOS 3: $FEV_1$ 50% or less of baseline

The formulation according to the invention is particularly advantageous in the prevention and treatment of pulmonary chronic graft rejection in single lung transplanted patients. More particularly, the poor outcome after single lung transplantation can be improved to an outcome which is comparable to the outcome after double lung transplantation. In a particular embodiment, the single lung transplanted patients suffered from chronic obstructive pulmonary disease or idiopathic pulmonary fibrosis before lung transplantation.

The invention further provides a method of preventing or treating pulmonary chronic graft rejection in single lung transplanted patients. The method involves (a) providing the cyclosporine liquid formulation as defined above, (b) providing a nebulizer capable of transforming the liquid formulation into an aerosol for inhalation, and (c) operating said nebulizer to aerosolize the said formulation. In a preferred embodiment, the method includes the use of an electronic vibrating membrane nebulizer. Preferably, the nebulizer comprises features for monitoring the time, date and duration of inhalation by the patient. According to a further embodiment, the nebulizer provided according to the method produces a signal in case of inappropriate nebulizer use or function. In another embodiment, a method of preventing or treating pulmonary chronic graft rejection in single lung transplanted patients is provided, wherein one or more active ingredients used in an oral standard immunosuppressive therapy after lung transplantation is administered in combination with the inhalable cyclosporine liquid formulation. Preferably, the one or more active ingredients used in standard immunosuppressive therapy after lung transplantation are administered in a dose which is lower than the dose used in standard immunosuppressive therapy after lung transplantation.

The following examples serve to illustrate the invention; however, these are not to be understood as restricting the scope of the invention.

EXAMPLES

Example 1: In Vitro Aerosol Characterization of Liquid CsA Formulation

A liposomal cyclosporine liquid formulation for inhalation consisting of the active substance CsA (Ph.Eur.) and the excipients lipoid S100, polysorbate 80, disodium edetate, disodium hydrogen phosphate dodecahydrate and sodium dihydrogen phosphate monohydrate was prepared. The formulation was adjusted to physiologically tolerable values of pH (6.5±0.2) and osmolality (350-450 mOsmol/kg).

An aerosol was generated using an eFlow® nebulizer with a 30XL configuration, using a mixing chamber with a volume of greater than 60 ml, in particular a mixing chamber with a volume of about 95 ml was used. The aerosol generated with this nebulizer was characterized using breath simulation, laser diffraction and impactor measurements. The results of these measurements are summarized in Table 1.

TABLE 1

Aerosol characteristics of a liposomal cyclosporine (L-CsA) formulation nebulized with an eFlow ® nebulizer with 30XL configuration

| | |
|---|---|
| Nominal drug amount [mg] | 15.0 ± 0.4 |
| MMD [μm] | 2.8 ± 0.1 |
| DD [%] | 75.9 ± 2.6 |
| RD [%, <5 μm] | 67.7 ± 2.8 |
| RD [%, <3.3 μm] | 46.7 ± 2.9 |

Values expressed as mean ± standard deviation; MMD = mass median diameter; DD = delivered dose (ex-mouthpiece); RD = respirable dose A delivered dose (DD) (amount ex-mouthpiece) of 76% and a respirable dose (RD) of droplets smaller than 3.3 μm of approximately 47% were achieved. Particles smaller than 3.3 μm have a high probability to deposit in the distal part of the lung which is regarded as the optimal drug deposition site for an efficacious lung graft protection. In general, aerosol droplets smaller than 5 μm have a high probability to deposit in the whole lung and should be considered for lung transplant protection to some extent as well. The respirable dose of droplets smaller than 5 μm was approximately 68%.

On the basis of these results, it can be concluded that for a nominal drug amount of mg, the corresponding delivered dose (in mg) will be approximately 7.6 mg CsA. The respirable dose (in mg) for droplets below 5 and 3.3 μm will be approximately 6.8 and 4.7 mg CsA, respectively.

Example 2: In Vitro Aerosol Characterization of Reconstituted CsA Formulation Sucrose was added as a lyoprotectant to the formulation described in Example 1. Afterwards, the formulation was lyophilized. Immediately before nebulization, the formulation was reconstituted with 2.3 ml 0.25% saline.

The liposome size was in the range of 40-100 nm (0.040-0.10 μm) with a polydispersity index of less than 0.40 after reconstitution.

The reconstituted formulation was nebulized with an eFlow® nebulizer with a 30XL configuration which had the same inhalation chamber as the nebulizer in Example 1, i.e. a mixing chamber with a volume greater than 60 ml, in particular a mixing chamber with a volume of about 95 ml was used. The results of the aerosol characterization data generated with the reconstituted formulation are shown in Table 2.

The results showed no substantial differences in comparison with the results obtained in Example 1.

TABLE 2

Aerosol characteristics of a reconstituted liposomal cyclosporine formulation nebulized with an eFlow ® nebulizer with 30XL configuration

| | |
|---|---|
| Fill volume [ml] | 2.5 |
| Nominal drug amount [mg] | 10.4 ± 0.0 |
| MMAD [μm] | 3.3 ± 0.1 |
| GSD | 1.5 ± 0.0 |
| DD [%] | 75.3 ± 2.6 |
| DD [mg] | 7.9 ± 0.3 |
| RD [%, <5 μm] | 65.3 ± 2.8 |
| RD [mg, <5 μm] | 6.8 ± 0.3 |
| RD [%, <3.3 μm] | 37.7 ± 2.2 |
| RD [mg, <3.3 μm] | 3.9 ± 0.2 |
| Nebulization time [min] | 7.4 ± 0.1 |

Values expressed as mean ± standard deviation; MMAD = mass median aerodynamic diameter; GSD = geometric standard deviation; DD = delivered dose (ex-mouthpiece); RD = respirable dose

Example 3: Clinical Trial with Inhaled Cyclosporine in the Prevention of BOS

Study Design

A phase III, multicentre, randomized, double blind, placebo controlled clinical trial was performed to investigate the efficacy and safety of aerosolized L-CsA versus aerosolized placebo in the prevention of BOS in lung transplanted patients.

Patients were allocated to receive twice daily either 5 mg/1.25 ml or 10 mg/2.5 ml L-CsA therapy, for single lung transplant (SLT) or double lung transplant (DLT) patients (L-CsA arm), respectively, or placebo (placebo arm) in addition to Standard of Care systemic immunosuppression.

In the L-CsA arm, double lung transplanted patients received the reconstituted L-CsA formulation described in Example 2. In single lung transplanted patients, the L-CsA dose was reduced by half compared to the dose for double lung transplanted patients since only half of the lung surface is available for drug deposition in single lung transplanted patients.

The placebo formulations used in the placebo arm of the study were lyophilized formulations with the same composition as the L-CsA lyophilized compositions, with the exception that they did not contain L-CsA. The same saline solution was used for reconstitution of the placebo formulation as was used for the L-CsA containing formulations.

Both the L-CsA formulations and the placebo formulations were nebulized using an eFlow® nebulizer with a 30XL configuration. A filter was placed on the exhaust valve of the inhalation chamber. Furthermore, the nebulizer was designed in such way that it could only be operated when a key card on which inhalation time and duration were monitored was introduced into the nebulizer.

The Standard of Care basic immunosuppression consisted of a triple drug therapy (TDT) of tacrolimus, prednisone, and mycophenolate mofetil. These drugs were administered orally. In the clinical trials, the Standard of Care therapy was followed according to centre-specific regimen, for example, target whole blood through level for tacrolimus (TAC) was between 8 to 12 ng/ml; the mycophenolate mofetil (MMF) was used between 1 to 3 g/d. Steroids were administered according to centre-specific protocols.

In summary, the patients were randomly assigned to one of the treatment arms as summarized in Table 3:

TABLE 3

Treatment arms of patients in clinical study

| | Single lung transplanted patients | Double lung transplanted patients |
|---|---|---|
| L-CsA arm | L-CsA 5 mg/1.25 ml twice daily for 96 weeks (24 months) plus Standard of Care systemic immunosuppression | L-CsA 10 mg/2.5 ml twice daily for 96 weeks (24 months) plus Standard of Care systemic immunosuppression |
| Placebo arm | Placebo 1.25 ml twice daily for 96 weeks (24 months) plus Standard of Care systemic immunosuppression | Placebo 2.5 ml twice daily for 96 weeks (24 months) plus Standard of Care systemic immunosuppression |

The treatment was commenced within 6 to 32 weeks following lung transplantation. Patients were monitored at regular intervals during 24 months for efficacy parameters and for all safety evaluations.

The primary efficacy endpoint of the study was BOS-free survival. Efficacy failure is the combined endpoint of occurrence of BOS or re-transplantation or death. BOS was defined as a sustained decrease in $FEV_1$ of at least 20% from the patient's maximum values in the absence of other causes and confirmed on the basis of histological markers for BO (Estenne M, et al. Bronchiolitis obliterans syndrome 2001: an update of the diagnostic criteria. *J Heart Lung Transplant* 2002; 21(3): 297-310). BOS was confirmed by at least two measurements which were taken at least three weeks apart. Maximal post-transplant values were the two best $FEV_1$ values taken at least three weeks apart. BOS-free survival was the time from first treatment to either first occurrence of BOS or re-transplantation or death.

The efficacy was further evaluated by measuring the following parameters (secondary endpoints):

- Forced expiratory volume in one second ($FEV_1$) at baseline, 12, 18 and 24 months after first treatment.
- Mean $FEV_1$ calculations were based on bi-monthly $FEV_1$ measurements according to current American Thoracic Society (ATS)/European Respiratory Society (ERS) spirometry guidelines. The baseline lung function, equivalent to 100% $FEV_1$, is defined as the average of the two highest $FEV_1$ measurements obtained at least three weeks apart without using a bronchodilator. All lung function parameters additional to $FEV_1$ were evaluated bi-monthly at each visit according to current ATS/ERS spirometry guidelines.
- Incidence of BOS at 12, 18 and 24 months after first treatment.
- Grading of BOS at 12, 18 and 24 months after first treatment.

Bronchiolitis obliterans syndrome (BOS) grading is as follows: Based on bi-monthly $FEV_1$ measurements, a BO evaluation was performed on a continuous basis. The definition of BO is according to modified BOS criteria from the publication of Estenne et al. (Estenne M, et al. Bronchiolitis obliterans syndrome 2001: an update of the diagnostic criteria. *J Heart Lung Transplant.* 2002; 21(3): 297-310) 2002, see above). The following definitions and criteria were applied:

- BOS 0: $FEV_1$>90% of baseline
- BOS 0-p: $FEV_1$ 81% to 90% of baseline
- BOS 1: $FEV_1$ 66% to 80% of baseline
- BOS 2: $FEV_1$ 51% to 65% of baseline
- BOS 3: $FEV_1$ 50% or less of baseline A BOS-related decrease in $FEV_1$ was determined by the average of two measurements made at least 3 weeks apart without the prior use of an inhaled bronchodilator. The date at which the patient enters the new BOS stage is the date of the first of the two measurements used to confirm the stage.

Incidence of lung graft loss until 12, 18 and 24 months after first treatment.

Any lung graft dysfunction leading to a complete or partial re-transplantation of lung tissue was regarded as lung graft loss.

Overall survival during the clinical trial period

Any case of fatality, irrespective of causality, was considered for survival analysis.

Analysis of the Results

The primary endpoint, BOS-free survival, was analysed by means of Kaplan-Meier survival analysis with stratification by single or double lung transplantation (SLT or DLT). Patients terminating their participation in the trial at any time and for any reason without experiencing an endpoint event were censored.

To perform the analyses, a Full Analysis Set (FAS) and a Per-Protocol Analysis Set (PPS) were defined. The FAS included all patients who received at least one dose of the investigational treatment. The PPS included all patients from the FAS without any major protocol violations that were considered to imperil the scientific aspects and interpretation of the study results (e.g. wrong inclusions, adherence of less than 75%, prohibited concomitant medications).

This resulted in the following patient disposition:

TABLE 4

Patient disposition

| | Full Analysis Set | | Per Protocol Analysis Set | |
|---|---|---|---|---|
| | L-CsA | Placebo | L-CsA | Placebo |
| Single lung transplanted patients | 23 | 17 | 12 | 12 |
| Double lung transplanted patients | 51 | 39 | 22 | 26 |

Results (Primary Endpoint)

The primary outcome result in the PPS population was based on the occurrence of BOS≥stage 1 (i.e. BOS 1, 2 or 3 as defined above) alone. The other co-primary endpoints, re-transplantation and death, did not contribute to the outcome.

A post-hoc BOS 0-p analysis showed that the deterioration of lung functions to BOS 0-p was postponed in the L-CsA groups compared with the placebo groups. This treatment effect was considered clinically meaningful as patients with BOS 0-p are at high risk of further deterioration to BOS stage 1 and higher over time. In the placebo groups, the incidence of BOS 0-p was approximately twice as high in the SLT patients as in the DLT patients. This means that the effect of L-CsA was more pronounced in the SLT patients.

Figure 2:
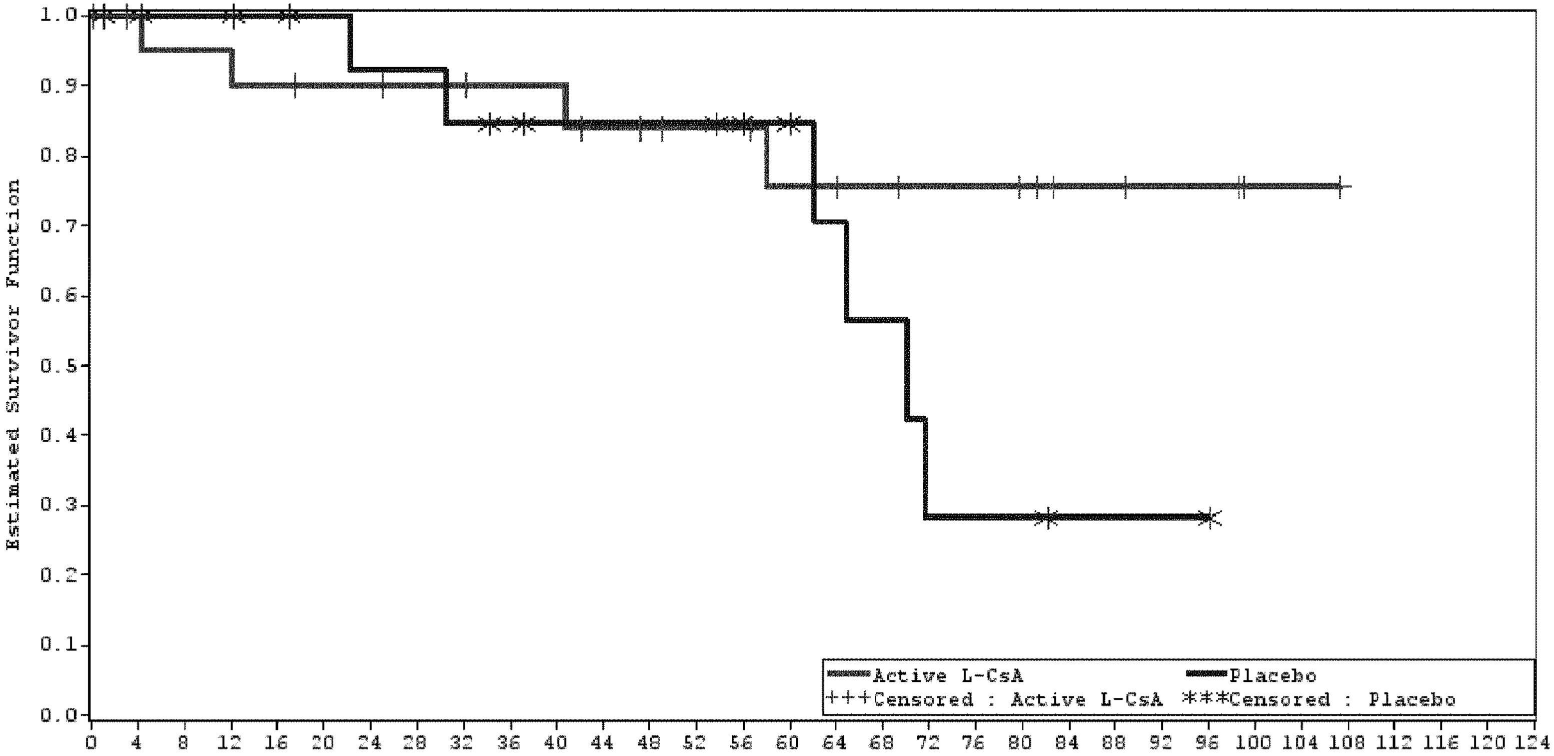
FIG. 2: Kaplan-Meier curve of BOS-free survival for single lung transplanted patients (full analysis set)
Figure 3:
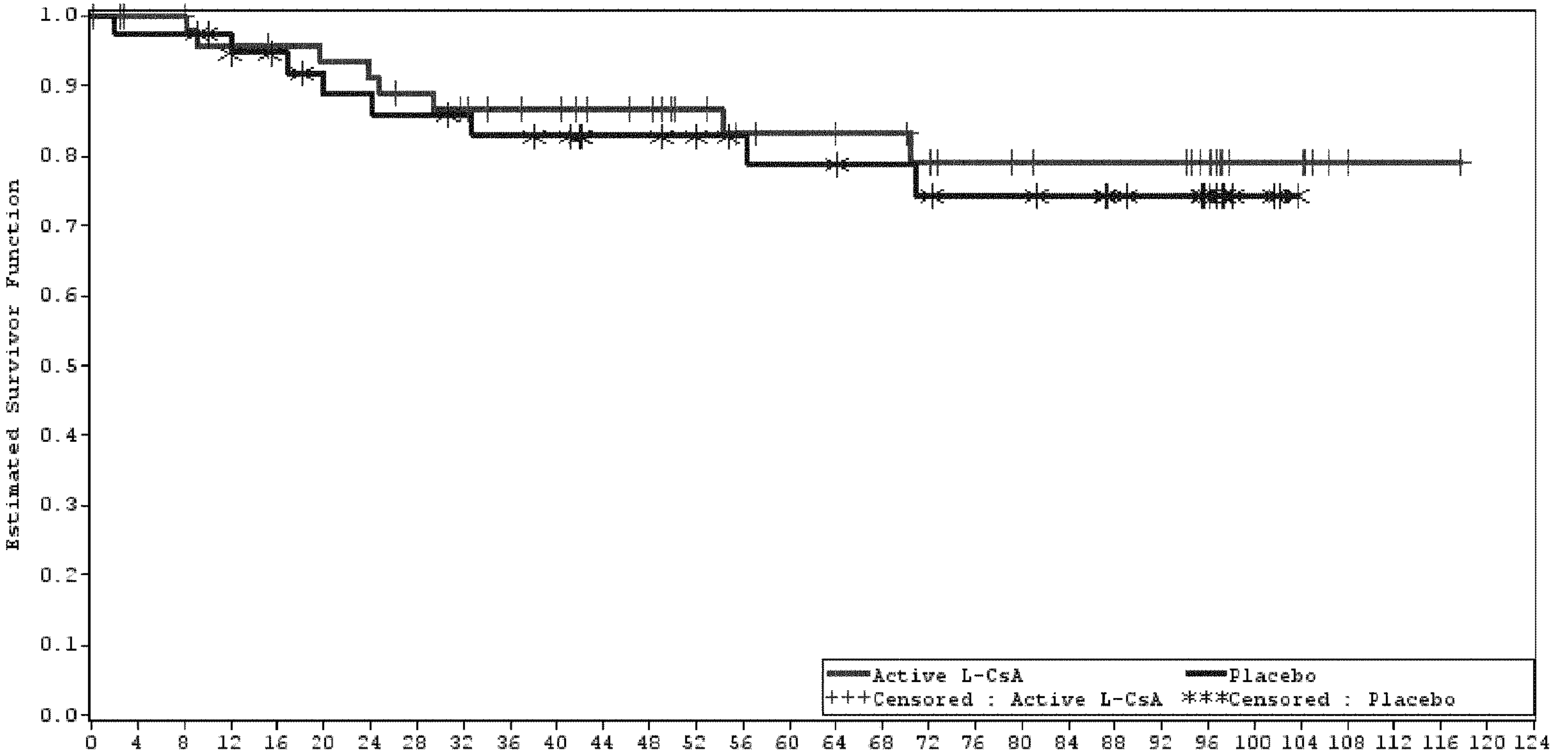
FIG. 3: Kaplan-Meier curve of BOS-free survival for double lung transplanted patients (full analysis set)

This becomes clear when comparing the Kaplan-Meier plots in FIGS. 1 to 3. From FIG. 1, where the BOS-free survival is shown for the FAS population, it is already clear that L-CsA postpones the occurrence of BOS compared with placebo. This can be seen from the growing difference between the decline of the curves when time progresses. However, when comparing FIGS. 2 and 3, where the BOS-free survival for SLT patients and DLT patients in the FAS population, respectively, are shown, it is obvious that the difference in decline of the curves in FIG. 1 is mainly caused by a difference in decline between the occurrence of BOS in the SLT patients treated with L-CsA or placebo.

Figure 4:
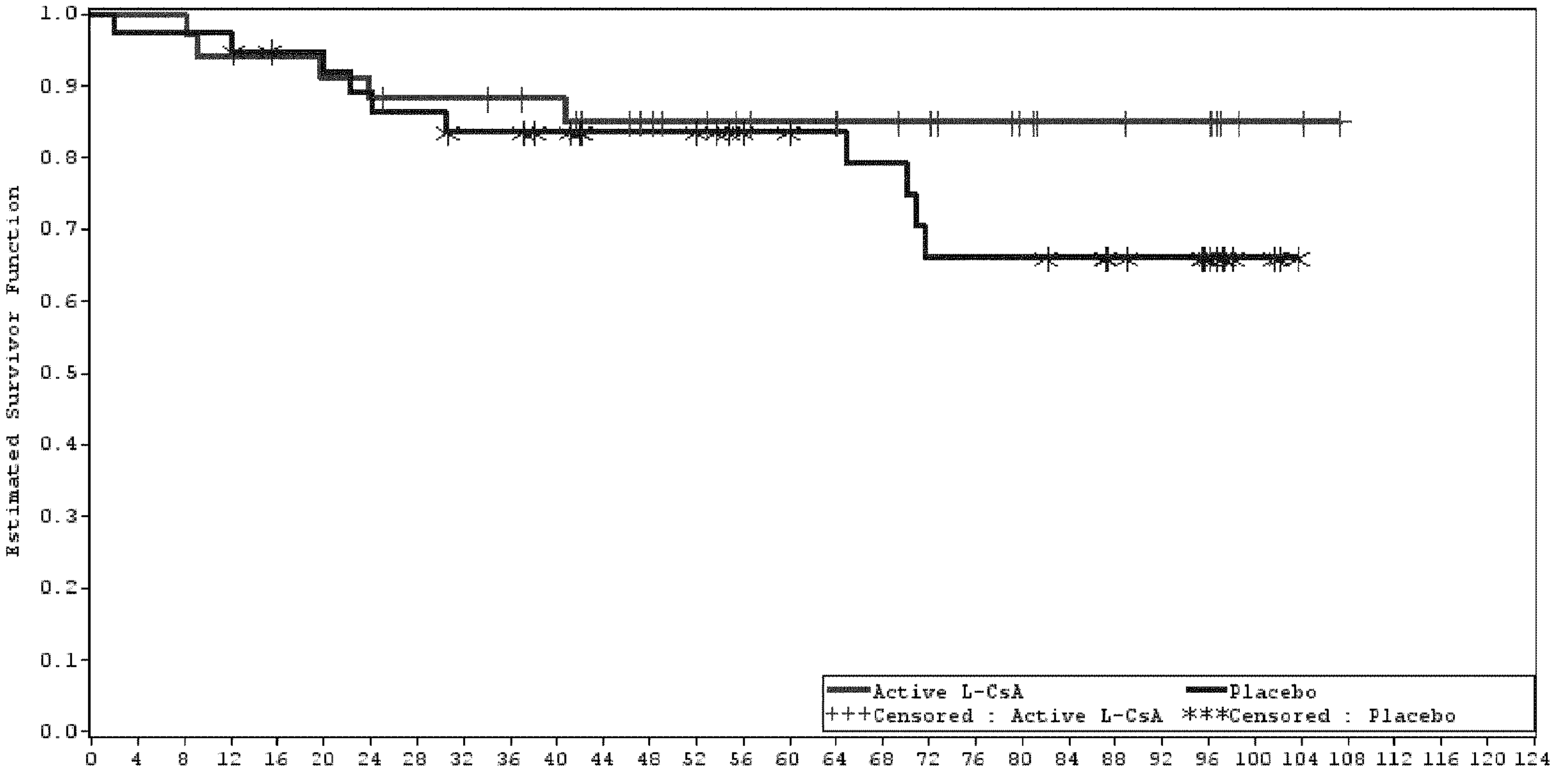
FIG. 4: Kaplan-Meier curve of BOS-free survival for all patients (per protocol analysis set)
Figure 5:
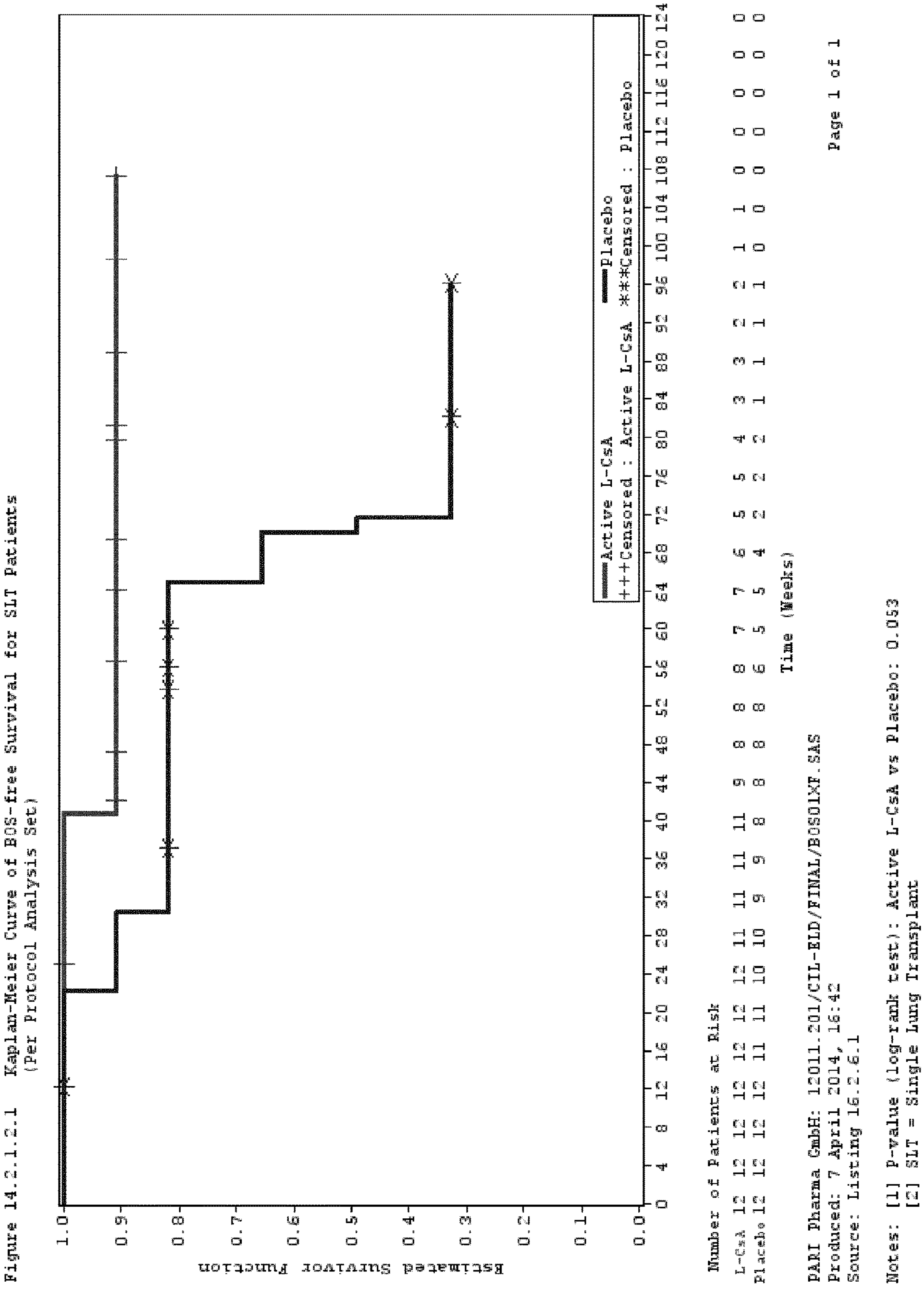
FIG. 5: Kaplan-Meier curve of BOS-free survival for single lung transplanted patients (per protocol analysis set)
Figure 6:
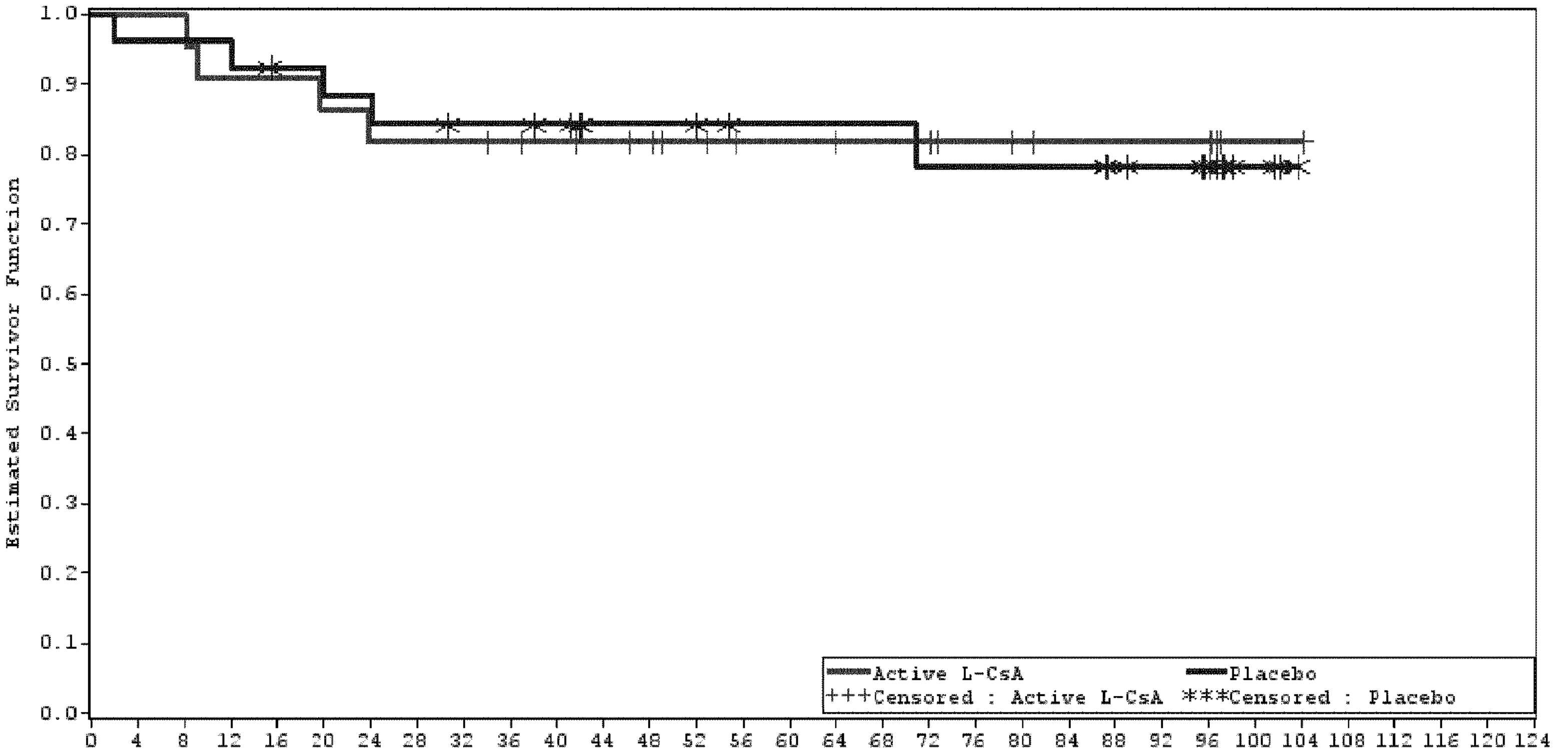
FIG. 6: Kaplan-Meier curve of BOS-free survival for double lung transplanted patients (per protocol analysis set)

This already shows that single lung transplanted patients benefit more from the L-CsA treatment than double lung transplanted patients. However, the difference becomes even clearer when analysing the PPS population (FIGS. 4 to 6). In this population, the log rank test comparing the L-CsA vs placebo groups approached statistical significance in SLT patients ($p=0.053$) favouring the L-CsA treatment, but was not statistically significant in DLT patients ($p=0.973$). The fact that the log rank test did not approach statistical significance in SLT patients when considering the FAS population ($p=0.191$) shows that patient adherence is a prerequisite for an efficacious therapy.

Results (Secondary Endpoints)

Figure 7:
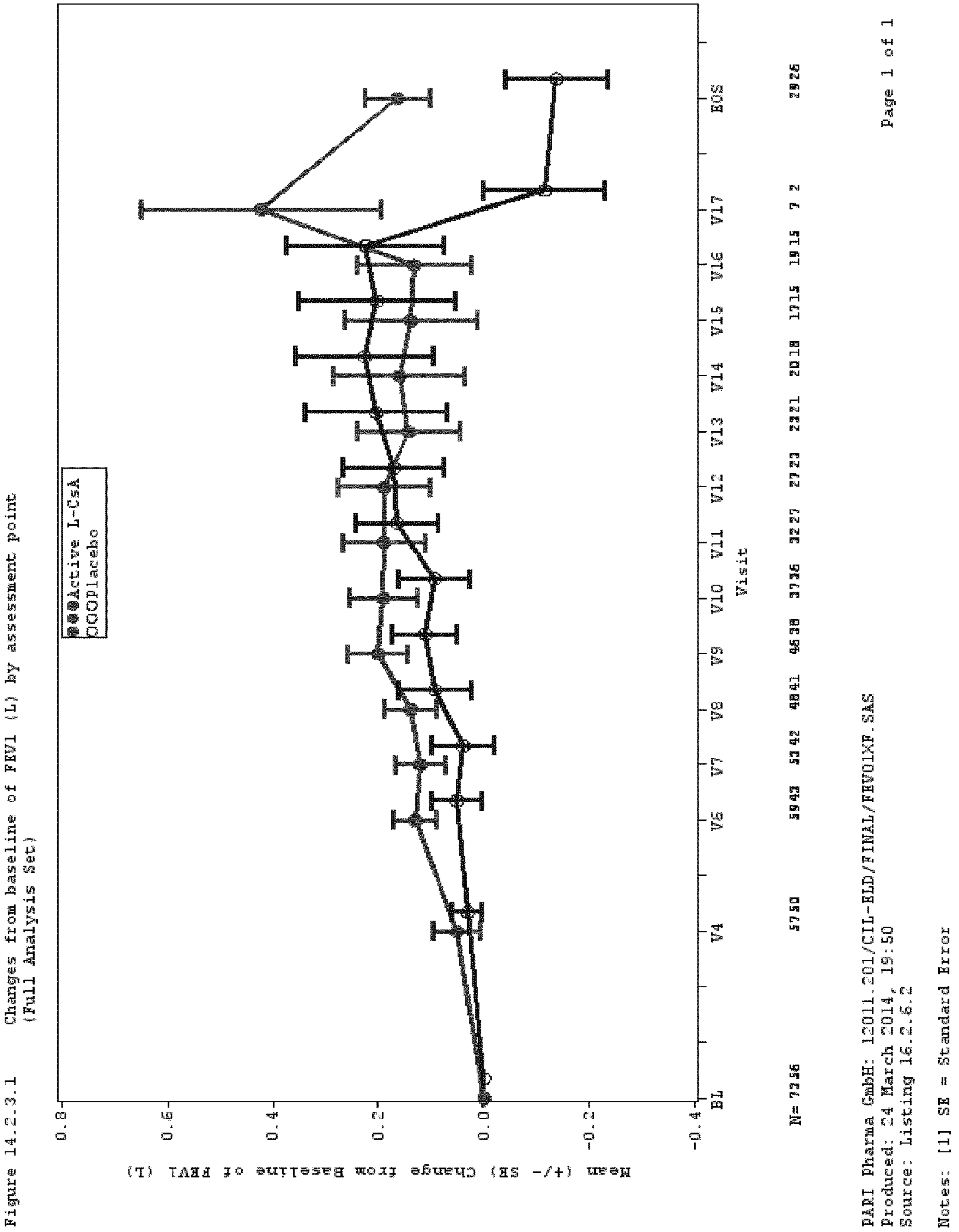
FIG. 7: Changes from baseline of $FEV_1$ (L) by assessment point for all patients (full analysis set)
Figure 8:
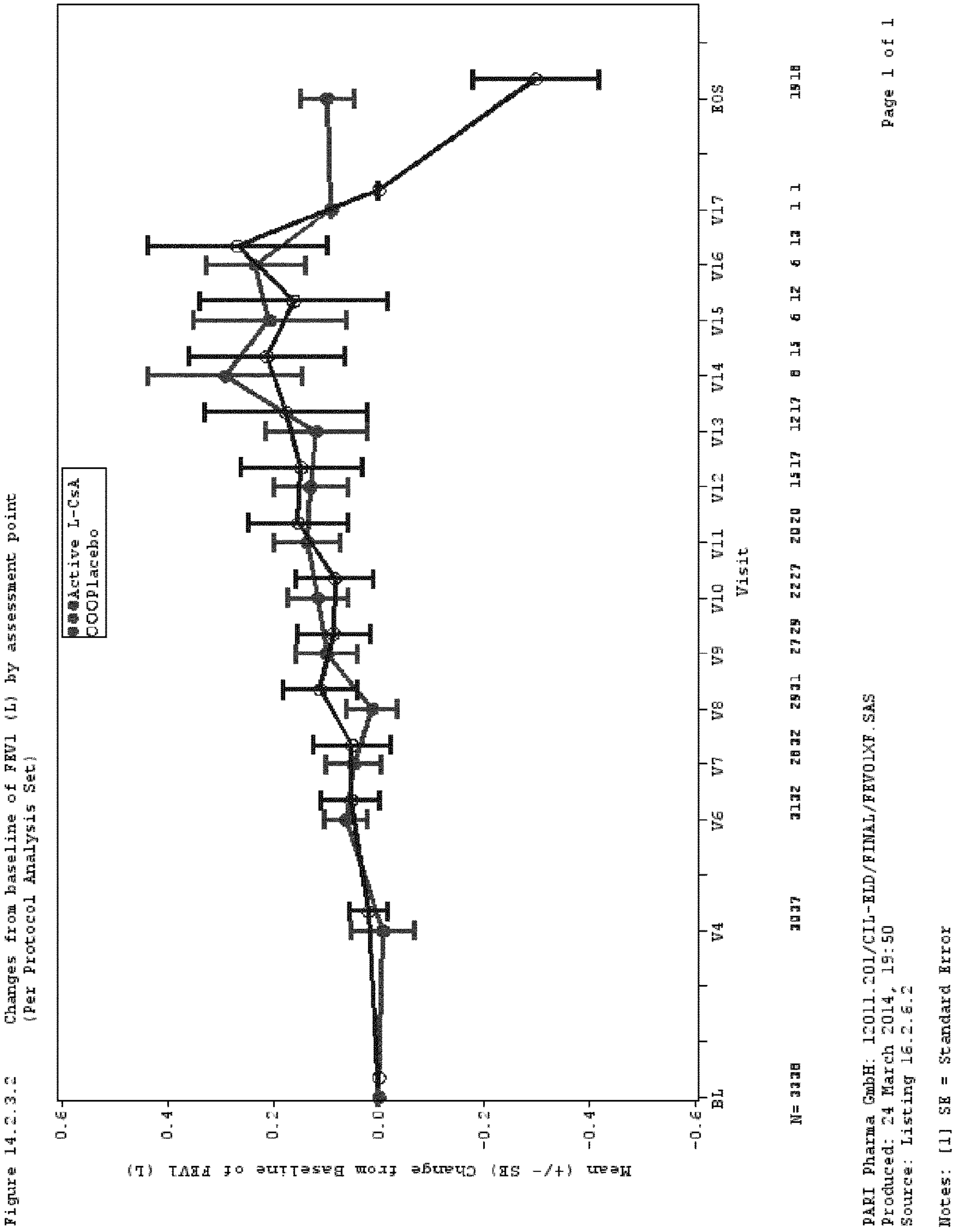
FIG. 8: Changes from baseline of $FEV_1$ (L) by assessment point for all patients (per protocol analysis set)
Figure 9:
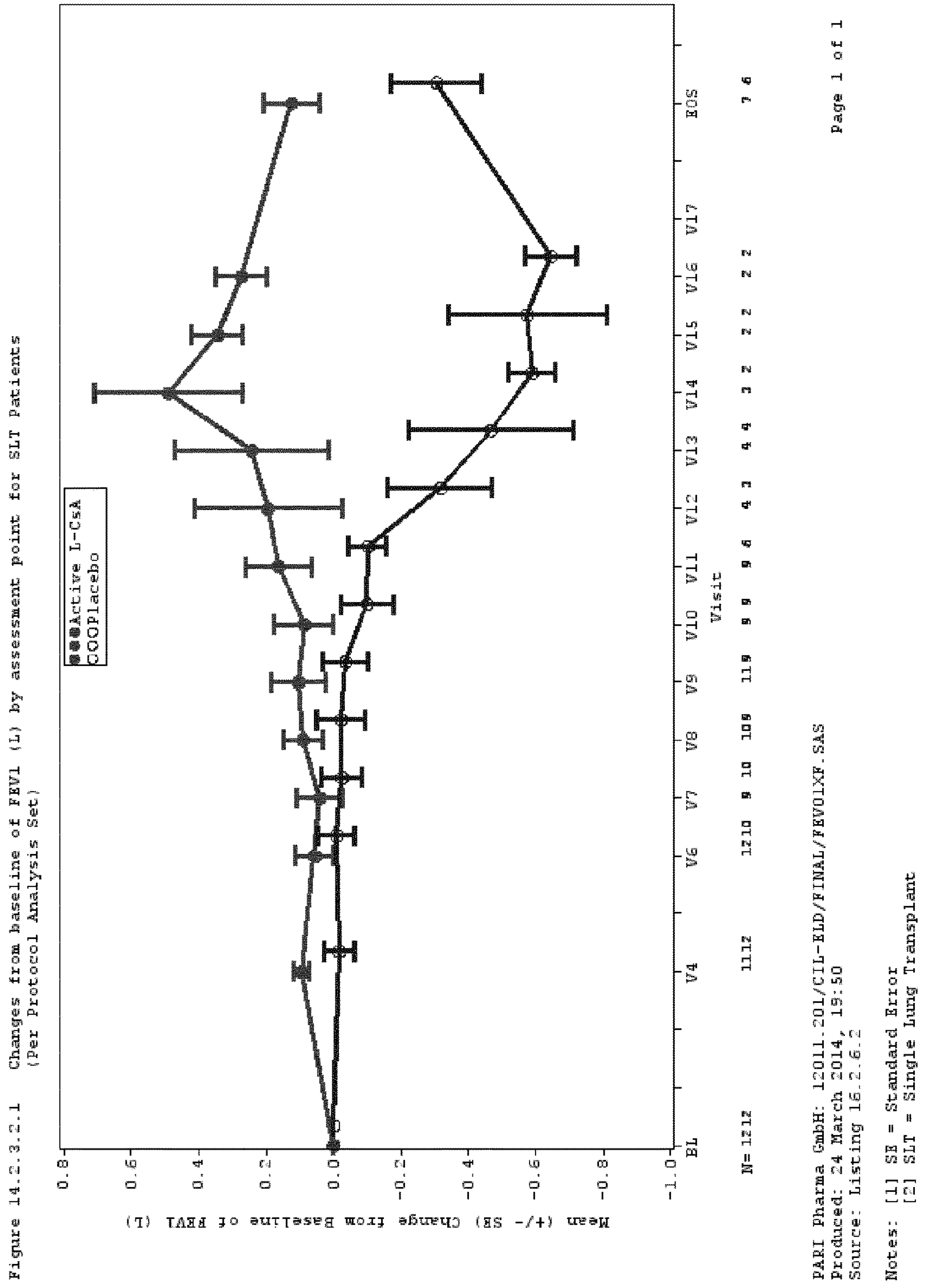
FIG. 9: Changes from baseline of $FEV_1$ (L) by assessment point for single lung transplanted patients (per protocol analysis set)
Figure 10:
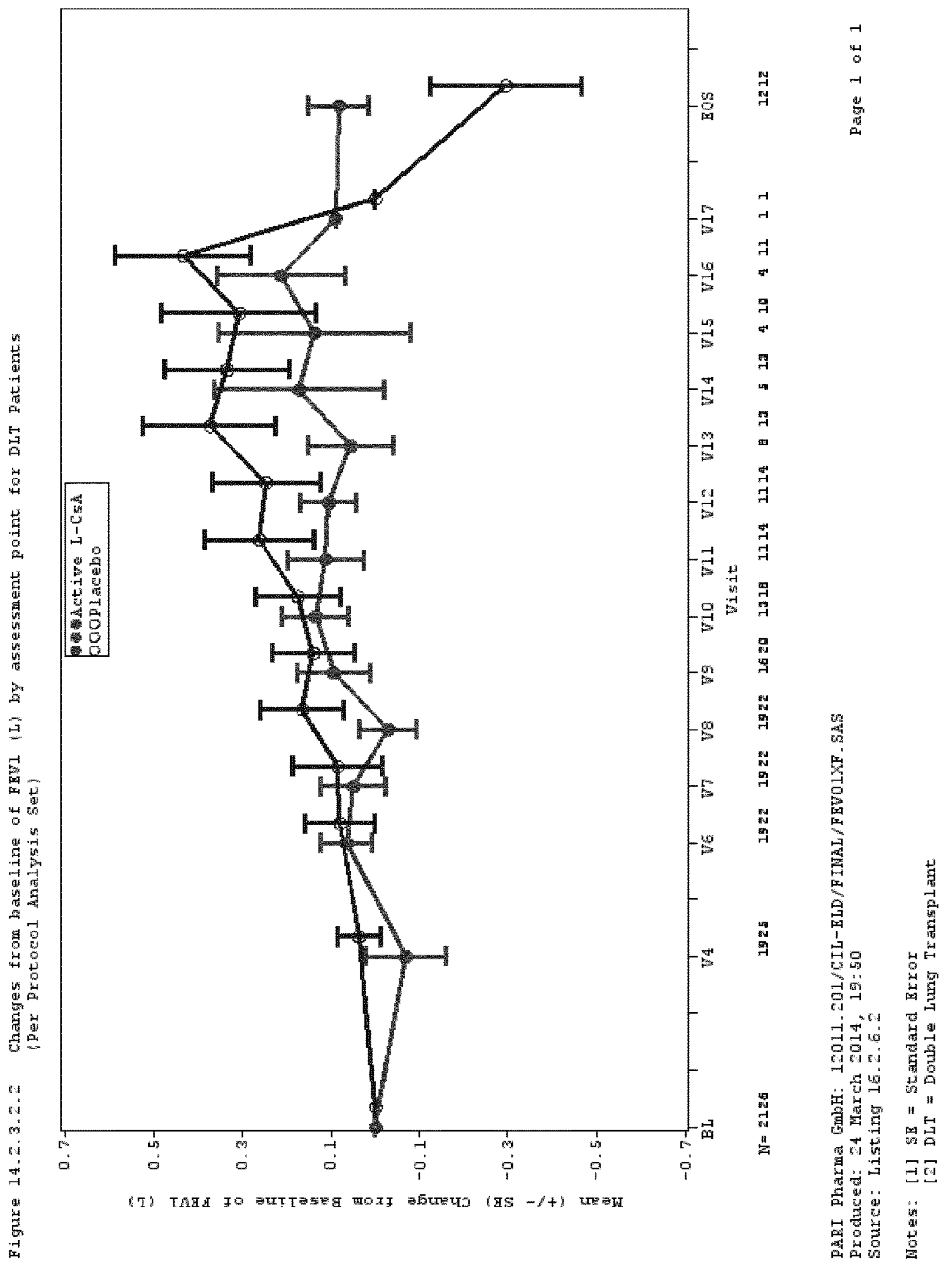
FIG. 10: Changes from baseline of $FEV_1$ (L) by assessment point for double lung transplanted patients (per protocol analysis set)

The mean changes from baseline of $FEV_1$ (L) tended to increase over time in patients of both the L-CsA and placebo groups, for both the FAS and PPS populations (FIGS. 7 and 8). The overall difference between the L-CsA and placebo groups was comparable when considering all patients. Treatment differences became obvious when analysing SLT and DLT patients separately. After one year of study participation, placebo patients in the SLT group deteriorated whereas L-CsA patients improved. The effect was more pronounced in the PPS population ($p=0.089$ at Month 24) than in the FAS population ($p=0.123$ at Month 24). This effect was not observed in the stratum of DLT recipients, neither in the FAS population, nor in the PPS population.

Figure 11:
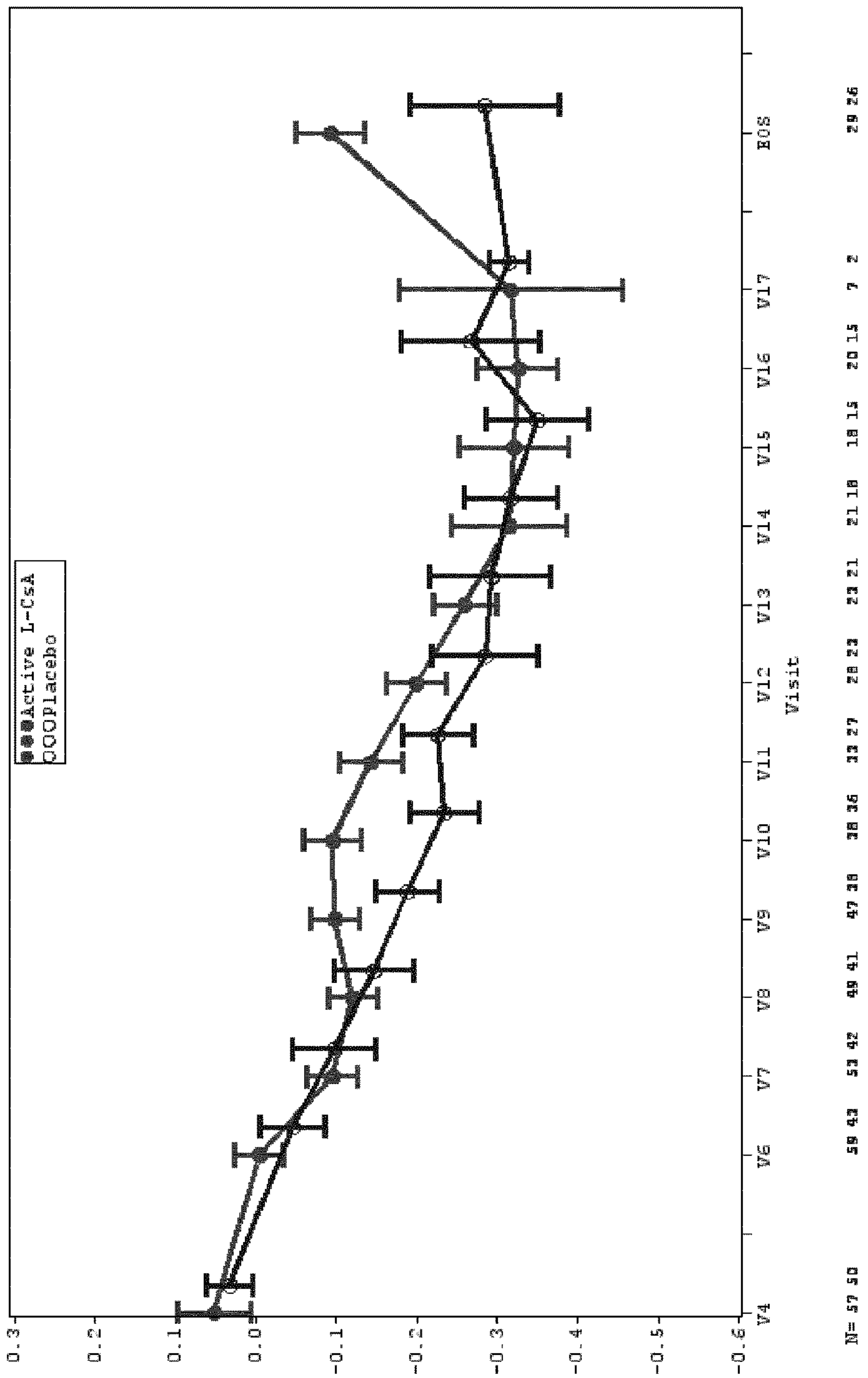
FIG. 11: Changes from maximum value of $FEV_1$ (L) by assessment point for all patients (full analysis set)

The mean changes from maximum value of $FEV_1$ (L) tended to decrease over time in patients randomized to both treatment groups, for both the PPS and FAS populations (FIGS. 11 and 12, respectively). The decrease was most distinct in the SLT patients of the PPS population (FIG. 13). The overall difference between the L-CsA and placebo groups showed statistical significance at Visit 10 (12 months) for the PPS population ($p=0.029$) and FAS population ($p=0.018$). Again, the differences between L-CsA and placebo treated patients became more prominent in the stratum of the SLT recipients (PPS and FAS). In SLT recipients treated with L-CsA, this parameter remained continuously stable over time whereas a sudden decrease was recorded in the placebo group starting one year after the beginning of the study. No difference could be recognized in the respective analyses of the DLT recipients (FIG. 14).

None of the patients in the L-CsA group experienced a lung graft loss (failure) during the study. In the placebo group, one patient lost his lung transplant before 12 months after the beginning of the study.

In the overall survival analysis of the PPS population, all patients in both treatment groups were alive until the end of their study participation, except one patient in the placebo group. In the FAS population, three patients in the L-CsA group and one patient in the placebo group deceased during their study participation.

Conclusions

Overall, the BOS events occurred earlier in the placebo group than in the L-CsA group. The major component of the composite endpoint was the occurrence of BOS. The fatal events occurred after the onset of BOS. Re-transplantations were not required at all.

An actuarial 2-year treatment difference of 19% in favour of L-CsA was found in the PPS population ($p=0.212$). This outcome was primarily the result of the unexpected large treatment difference observed in the subpopulation of SLT recipients (actuarial 2-year difference=58%) which reached borderline statistical significance (p=0.053). Such difference is regarded as clinically relevant.

Example 4: Clinical Trial with Inhaled Cyclosporine in the Treatment of BOS

This further trial is an investigator initiated, single centre, open-label, pilot study investigating the addition of liposomal CsA (L-CsA) for inhalation to Standard of Care therapy versus Standard of Care therapy alone in the treatment of bronchiolitis obliterans syndrome (BOS) following lung transplantation.

This study aims at patients who received single or double lung transplantation and developed clinically diagnosed BOS grade 1 or 2 within 4 weeks prior to study entry.

The invention claimed is:

1. A method of preventing or treating pulmonary chronic graft rejection in single lung transplanted patients comprising administering to a patient in need thereof a liposomal cyclosporine liquid formulation as an aerosol for inhalation;

wherein the formulation is administered as an aerosol to said patient at a daily dosage of cyclosporine A ranging between 2 and 30 mg, wherein the patient is co-administered one or more active ingredients used in standard immunosuppressive therapy after lung transplantation, wherein the one or more active ingredients constitute a standard of care systemic immunosuppression regimen;

and wherein the patient is a human patient.

2. The method according to claim 1, wherein the daily dosage is 10 mg.

3. The method according to claim 1, wherein the patient is a human patient of higher age.

4. The method according to claim 1, wherein the formulation contains the cyclosporine at a concentration of 1 up to 5 mg/ml.

5. The method according to claim 1, wherein the volume of a unit dose of the formulation is 1 to 3 ml.

6. The method according to claim 1, wherein the formulation is aerosolized with an electronic vibrating membrane nebulizer.

7. The method according to claim 1, wherein the formulation is aerosolized with a nebulizer that comprises features for monitoring the time, date and duration of inhalation by the patient.

8. The method according to claim 1, wherein the formulation is inhaled as intended in at least 65% of the intended inhalation cycles.

9. The method according to claim 1, wherein the formulation is inhaled as intended in at least 75% of the intended inhalation cycles.

10. The method according to claim 1, wherein the time, date and duration of inhalation by the patient are monitored and if the inhalation of the formulation is not carried out or not finished as intended in at least 65% of the intended inhalation cycles, then the monitoring system produces a signal indicating insufficient patient adherence.

11. The method according to claim 1, wherein the formulation contains the cyclosporine at a concentration of about 4 mg/mL.

12. The method according to claim 1, wherein the volume of a unit dose of the formulation is about 1.25 mL or about 2.5 mL.

13. The method according to claim 1, wherein the one or more active ingredients is/are selected from the group consisting of tacrolimus or cyclosporine, other than the liposomal cyclosporine liquid formulation; mycophenolate mofetil or azathioprine; and corticosteroids.

14. The method according to claim 1, wherein the pulmonary chronic graft rejection is characterized by bronchiolitis obliterans syndrome.

15. The method according to claim 1, wherein the pulmonary chronic graft rejection is characterized by a reduction of the forced expiratory volume in one second (FEV1) of at least 20% from the patient's maximum values.

16. The method according to claim 1, wherein the formulation is used in single lung transplanted patients who suffered from emphysema, fibrosis, and/or chronic obstructive pulmonary disease before the lung transplantation.

17. The method according to claim 16, wherein the fibrosis is idiopathic pulmonary fibrosis.

18. The method according to claim 13, wherein the one or more active ingredients is/are administered by oral administration.

19. The method according to claim 7, wherein the nebulization time of a unit dose of the formulation is not more than about 10 minutes, or not more than about 5 minutes.

20. The method according to claim 7, wherein the unit dose is a 5 mg dose, and the nebulization time is not more than about 5 minutes.

21. The method according to claim 1, wherein the one or more active ingredients are selected from immunoglobulins, cell-cycle inhibitors, calcineurin inhibitors, mTor inhibitors, and corticosteroids.

22. The method according to claim 1, wherein the one or more active ingredients constitute a triple drug therapy comprising a calcineurin inhibitor, a cell-cycle inhibitor, and a corticosteroid.

23. The method according to claim 1, wherein the one or more active ingredients is/are selected from azathioprine, mycophenolic acid or its salts, cyclosporine other than the aerosol cyclosporine liquid formulation, tacrolimus, sirolimus, everolimus, hydrocortisone, methylprednisolone, prednisolone, or any of their salts or esters.

24. The method according to claim 1, wherein the method is carried out to prevent or delay the occurrence of bronchiolitis obliterans after transplantation compared to treatment with the one or more active ingredients used in standard immunosuppressive therapy after lung transplantation alone.

25. The method according to claim 1, wherein the method is carried out for a period of treatment of at least 12 months.

26. The method according to claim 1, wherein the method is carried out for a period of treatment of at least 18 months.

27. The method according to claim 1, wherein the method is carried out for a period of treatment of at least 24 months.

28. The method according to claim 1, wherein the formulation is administered once or twice daily.

29. The method according to claim 1, wherein the formulation is administered twice daily.

* * * * *